US007365084B2

(12) United States Patent
Stapper et al.

(10) Patent No.: US 7,365,084 B2
(45) Date of Patent: Apr. 29, 2008

(54) CYCLOALKYL-SUBSTITUTED AMINO ACID DERIVATIVES, PROCESSES FOR THEIR PREPARATION AND THEIR USE AS PHARMACEUTICALS

(75) Inventors: Christian Stapper, Mainz (DE); Stefanie Keil, Hofheim (DE); Heiner Glombik, Hofheim (DE); Eugen Falk, Frankfurt (DE); Jochen Goerlitzer, Frankfurt am Main (DE); Dirk Gretzke, Frankfurt (DE); Hans-Ludwig Schaefer, Hochheim (DE); Wolfgang Wendler, Selters (DE)

(73) Assignee: SanoFi-Aventis Deutschland GmbH, Frankfurt (DE)

( * ) Notice: Subject to any disclaimer, the term of this patent is extended or adjusted under 35 U.S.C. 154(b) by 520 days.

(21) Appl. No.: 10/788,997

(22) Filed: Feb. 27, 2004

(65) Prior Publication Data
US 2005/0215596 A1 Sep. 29, 2005

Related U.S. Application Data

(60) Provisional application No. 60/487,510, filed on Jul. 15, 2003.

(30) Foreign Application Priority Data
Feb. 27, 2003 (DE) .................. 103 08 355

(51) Int. Cl.
C07D 413/02 (2006.01)
C07D 263/30 (2006.01)
A61K 31/4439 (2006.01)
A61K 31/422 (2006.01)

(52) U.S. Cl. .................. 514/340; 514/374; 548/235
(58) Field of Classification Search ................ 514/374; 548/235
See application file for complete search history.

(56) References Cited

U.S. PATENT DOCUMENTS

| 6,221,633 | B1 | 4/2001 | Ertl et al. |
| 6,221,897 | B1 | 4/2001 | Frick et al. |
| 6,245,744 | B1 | 6/2001 | Frick et al. |
| 6,277,831 | B1 | 8/2001 | Frick et al. |
| 6,342,512 | B1 | 1/2002 | Kirsch et al. |

FOREIGN PATENT DOCUMENTS

| EP | 0 462 884 A1 | 12/2001 |
| WO | WO 94/18183 | 8/1994 |
| WO | WO 94/18184 | 8/1994 |
| WO | WO 96/38428 | 12/1996 |
| WO | WO 97/26265 | 7/1997 |
| WO | WO 97/41097 | 11/1997 |
| WO | WO 98/08871 | 3/1998 |
| WO | WO 98/19998 | 5/1998 |
| WO | WO 99/03861 | 1/1999 |
| WO | WO 99/15525 | 4/1999 |
| WO | WO 99/61431 | 12/1999 |
| WO | WO 99/62871 | 12/1999 |
| WO | WO 99/62872 | 12/1999 |
| WO | WO 99/67278 | 12/1999 |
| WO | WO 99/67279 | 12/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |
| WO | WO 01/21602 A1 | 3/2001 |
| WO | WO 01/40169 A1 | 6/2001 |
| WO | WO 01/40171 A1 | 6/2001 |
| WO | WO 01/72290 A2 | 10/2001 |
| WO | WO 01/81327 A1 | 11/2001 |
| WO | WO 01/83451 A1 | 11/2001 |
| WO | WO 01/85695 A1 | 11/2001 |
| WO | WO 01/91752 A1 | 12/2001 |
| WO | WO 01/94300 A1 | 12/2001 |
| WO | WO 02/38541 A1 | 5/2002 |
| WO | WO 02/50027 | 6/2002 |
| WO | WO 02/096864 A1 | 12/2002 |
| WO | WO 02/100403 A1 | 12/2002 |
| WO | WO 03/020269 | 3/2003 |
| WO | WO 03/040174 A2 | 5/2003 |
| WO | WO 03/084922 | 10/2003 |
| WO | WO 03/084923 | 10/2003 |
| WO | WO 03/104188 | 12/2003 |

OTHER PUBLICATIONS

Asakawa A et al., Cocaine-Amphetamine-Regulated Transcript Influences Energy Metabolism Anxiety and Gastric Emptying in Mice, Hormone and Metabolic Research; vol. 33(9); 2001; pp. 554-558.
Berger Joel et al., The Mechanisms of Action of PPARs, Annul. Rev. Med.; vol. 53; 2002; pp. 409-435.
Fruchart Jean-Charles et al., PPARs, Metabolic Disease and Atherosclerosis, Pharmacological Research; vol. 44, No. 5; 2001; pp. 345-352.
Kersten Sander et al et al., Roles of PPARs in Health and Disease, Nature; vol. 405; May 25, 2000; pp. 421-424.
Kliewer Steven A et al., Peroxisome Proliferator-Activated Receptors: From Genes to Physiology, Recent Prog. Horm Res.; vol. 56; 2001; pp. 239-263.
Lee Daniel W et al., Leptin agonists as a potential approach to the treatment of obesity, Drugs of the Future; vol. 26(9); 2001; pp. 873-881.
Motojima Kiyoto, Peroxisome Proliferator-Activated Receptor (PPAR): Structure, Mechanisms of Activation and Diverse Functions, Cell Structure and Function; vol. 18; 1993; pp. 267-277.

(Continued)

Primary Examiner—Kamal A. Saeed
(74) Attorney, Agent, or Firm—Barbara E. Kurys

(57) ABSTRACT

Provided herein are cycloalkyl-substituted amino acid derivatives, processes for their preparation and their use as pharmaceuticals.

17 Claims, No Drawings

OTHER PUBLICATIONS

Okada Hiroshi et al., Synthesis and Antitumor Activities of Prodrugs of Benzoylphenylureas, Chem. Pharm. Bull.; vol. 42,(1); 1994; pp. 57-61.

Pineda Torra Ines et al., Peroxisome Proliferator-activated Receptors: from Transcriptional Control to Clinical Practice, Curr. Opin. Lipidol; vol. 12; 2001; pp. 245-254.

Pineda Torra Ines et al., Peroxisome proliferator-activated receptor alpha in metabolic disease, inflammation, atherosclerosis and aging, Curr. Opin. Lipidol; vol. 10; 1999; pp. 151-159.

Vidal-Puig A et al., Regulation of PPAR y Gene Expression by Nutrition and Obesity in Rodents, J. Clin. Invest.; vol. 97, No. 11, 1996; pp. 2553-2561.

Wilson Timothy M. et al., The PPARs: From Orphan Receptors to Drug Discovery, Journal of Medicinal Chemistry; vol. 43, No. 4; 2000; pp. 527-550.

Zunft H,. J. F. et al., Carob Pulp Preparation for Treatment of Hypercholesterolemia, Advances in Natural Therapy; vol. 18, No. 5; Sep.-Oct. 2001; pp. 230-236.

```
                       SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 1
cggagtactg tcctccgag                                              19

<210> SEQ ID NO 2
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 2
ctcggaggac agtactccg                                              19
```

CYCLOALKYL-SUBSTITUTED AMINO ACID DERIVATIVES, PROCESSES FOR THEIR PREPARATION AND THEIR USE AS PHARMACEUTICALS

DOMESTIC PRIORITY CLAIM

This Application claims priority from U.S. Provisional Application No. 60/487,510 filed on Jul. 15, 2003.

PRIORITY CLAIM

This Application claims priority from German Application No. 10308355.3 filed on Feb. 27, 2003.

FIELD OF INVENTION

The invention relates to cycloalkyl-substituted amino acid derivatives and to their physiologically acceptable salts and physiologically functional derivatives.

BACKGROUND OF THE INVENTION

Compounds of a similar structure have already been described in the prior art for the treatment of hyperlipidemia and diabetes (WO 2000/64876).

The citation of any reference herein should not be construed as an admission that such reference is available as "Prior Art" to the instant application.

SUMMARY OF THE INVENTION

The present invention extends to a compound of the formula I

I in which:
Ring A is $(C_3-C_8)$-cycloalkanediyl or $(C_3-C_8)$-cycloalkenediyl, wherein one or more of the carbon atoms of the $(C_3-C_8$-cycloalkanediyl or $(C_3-C_8)$ cycloalkenediyl rings may be replaced by oxygen atoms;
R1, R2 are independently of each other H, F, Cl, Br, $CF_3$, $OCF_3$, $(C_1-C_6)$-alkyl, O—$(C_1-C_6)$-alkyl, $SCF_3$, $SF_5$, $OCF_2$—$CHF_2$, $(C_6-C_{10})$-aryl, $(C_6-C_{10})$-aryloxy, OH, $NO_2$; or
R1 and R2 together with the phenyl, pyridine, 1H-pyrrole, thiophene or furan ring form fused, partially or unsaturated bicyclic $(C_6-C_{10})$-aryl, $(C_5-C_{11})$-heteroaryl;
R3 is H, $(C_1-C_6)$-alkyl, $(C_3-C_8)$-cycloalkyl, $(C_1-C_3)$-alkyl-$(C_3-C_8)$-cycloalkyl, phenyl, $(C_1-C_3)$-alkyl-phenyl, $(C_5-C_6)$-heteroaryl, $(C_1-C_3)$-alkyl-$(C_5-C_6)$-heteroaryl or $(C_1-C_3)$-alkyl which is fully or partially substituted by F;
W is CH or N if o=1;
W is O, S or NR10 if o=0;
X is $(C_1-C_6)$-alkanediyl, wherein one or more carbon atoms of the $(C_1-C_6)$-alkanediyl group may be replaced by oxygen atoms;
n is 0-2;
R4 is H or $(C_1-C_6)$-alkyl;
R5 is H or $(C_1-C_6)$-alkyl;
R6 is H, $(C_1-C_6)$-alkyl or F;
R7 is H; F; $(C_1-C_6)$-alkoxy; $(C_2-C_6)$-alkenyl; $(C_2-C_6)$-alkynyl; $(C_3-C_8)$-cycloalkyl; phenyl which may be unsubstituted or substituted by one or more radicals from the group consisting of hydroxy, $(C_1-C_6)$-alkoxy, F and $CF_3$; $(C_1-C_6)$-alkyl which may be unsubstituted or substituted by one or more radicals selected from the group consisting of hydroxyl, phenyl, $(C_5-C_{11})$-heteroaryl, $(C_1-C_6)$-alkoxy and NR11R12;
with the proviso that R7 is not NR11R12 or $(C_1-C_6)$-alkoxy if R6=F;
R7 and R9 together with the atoms that carry form pyrrolidine or piperidine if n=0;
R6 and R7 together with the carbon atom that carries them are $(C_3-C_8)$-cycloalkyl;
R8 is H, $(C_1-C_6)$-alkyl;
R9 is H, $(C_1-C_6)$-alkyl, $(C_2-C_6)$-alkenyl, $(C_2-C_6)$-alkynyl, $(C_1-C_4)$-alkyl-$(C_6-C_{10})$-aryl, $(C_1-C_4)$-alkyl-$(C_5-C_{11})$-heteroaryl, $(C_1-C_4)$-alkyl-O—$(C_1-C_4)$-alkyl, phenyl-$(C_1-C_4)$-alkyl, $(C_5-C_6)$-heteroaryl-$(C_1-C_4)$-alkyl;
R10 is H, $(C_1-C_6)$-alkyl-phenyl, $(C_1-C_6)$-alkyl;
R11 is H, $(C_1-C_6)$-alkyl-phenyl, $(C_1-C_6)$-alkyl; and
R12 is H, $(C_1-C_6)$-alkyl-phenyl, $(C_1-C_6)$-alkyl,
a physiologically acceptable salt of the compound;
a solvate of the compound; and
a physiologically functional derivative of the compound.

Furthermore, the present invention extends to a compound of the formula I above in which
Ring A is $(C_3-C_8)$-cycloalkanediyl or $(C_3-C_8)$-cycloalkenediyl, wherein one carbon atom of the $(C_3-C_8)$-cycloalkanediyl ring or $(C_3-C_8)$-cycloalkenediyl ring one carbon atom may be replaced by an oxygen atom;
X is $(C_1-C_6)$-alkanediyl, wherein the $C_1$ or $C_2$ carbon atom (to Ring A) of the $(C_1-C_6)$-alkanediyl group may be replaced by an oxygen atom.

In addition, the present invention extends to a compound of formula I above, wherein one or more radicals are as defined below:
Ring A is cyclohexane-1,3-diyl; or
R1 is F, Br, $CF_3$, $OCF_3$, (C1-C6)-alkyl, O—(C1-C6)-alkyl, phenyl; or
those in which the substituent
R1 is in the meta- or in the para-position; or
R2 is hydrogen; or
R1 and R2 together with the phenyl ring form a naphthyl; or
R3 is H, $(C_1-C_6)$-alkyl, $(C_3-C_8)$-cycloalkyl, $(C_1-C_3)$-alkyl-$(C_5-C_6)$-cycloalkyl, phenyl, $(C_1-C_3)$-alkyl-phenyl; or
W is CH if o=1; or
X is $CH_2$—O or $CH_2$—O—$CH_2$; or
n is 0; or
R6 is H, $(C_1-C_6)$-alkyl; or
R6 and R7 together with the carbon atom that carries them are $(C_3-C_6)$-cycloalkyl, in particular cyclopentyl;
R7 is $(C_1-C_6)$-alkyl, where alkyl may be unsubstituted or substituted by one or more radicals selected from the group consisting of hydroxyl, phenyl, $(C_5-C_{11})$-heteroaryl, $(C_1-C_6)$-alkoxy and NR11R12, where
R11 and R12 are H or $(C_1-C_6)$-alkyl;
a physiologically acceptable salt of the compound;
a solvate of the compound; and
a physiologically functional derivative of the compound.

Furthermore, the present invention extends to a compound of the formula I, a physiologically acceptable salt of the compound, a solvate of the compound, and a physiologically functional derivative of the compound, in which R7 is $(C_1-C_4)$-alkyl, $(C_1-C_4)$-alkyl-O—$(C_1-C_4)$-alkyl or benzyl;
very particularly
R7 is $(C_1-C_4)$-alkyl or benzyl.

Also, the present invention extends to a compound of the formula I, a physiologically acceptable salt of the compound, a solvate of the compound, and a physiologically functional derivative of the compound, in which
Ring A is cis-cyclohexane-1,3-diyl
R1 is Br, $CF_3$, $OCF_3$, $(C_1-C_6)$-alkyl, O—$(C_1-C_6)$-alkyl;
R2 is H, $(C_1-C_6)$-alkyl, O—$(C_1-C_6)$-alkyl or
R1 and R2 together with the phenyl ring form a naphthyl;
R3 is $CF_3$, $(C_1-C_6)$-alkyl, $(C_3-C_8)$-cycloalkyl, phenyl;
W is CH if o=1;
X is $CH_2O$, $CH_2$—O—$CH_2$;
n is 0
R6 is H or $(C_1-C_6)$-alkyl;
R7 is $(C_1-C_6)$-alkyl, where alkyl may be unsubstituted or substituted by phenyl;
R7 and R9 together with the atoms that carry them are pyrrolidine if n=0;
R6 and R7 together with the carbon atom that carries them are $(C_3-C_6)$-cycloalkyl;
R8 is H; and
R9 is H; $(C_1-C_6)$-alkyl or benzyl.

The alkyl radicals in the substituents R1, R2, R3, R4, R5, R6, R7, R8, R9, R10, R11 and R12 may be either straight-chain or branched.

In another embodiment, the present invention extends to a method of treating and/or preventing a disorder or condition in a patient comprising administering a therapeutically effective amount of a compound of formula I described above, a physiologically effective salt of a compound of formula I above, a solvate of a compound of formula I described above, a physiologically acceptable derivative of a compound of formula I above, or even a combination thereof to the patient. Particular examples of disorders and conditions that can be treated and/or prevented with the administration of a compound of the present invention are described infra.

The present invention further extends to a method for treating and/or preventing a disorder of fatty acid metabolism or glucose utilization in a patient, comprising administering a therapeutically effective amount of a compound of the formula I above.

Moreover, the present invention extends to a method for treating and/or preventing a disorder involving insulin resistance in a patient, comprising administering a therapeutically effective amount of a compound of the formula I above to the patient.

The present invention also extends to a method for treating and/or preventing diabetes mellitus and its sequelae in a patient, comprising administering a therapeutically effective amount of a compound of the formula I to the patient.

In another emobidment, the present invention extends to a method for treating and/or preventing dyslpidemias and their sequelae in a patient, comprising administering a therapeutically effective amount of a compound of formula I above to the patient.

Similarly, the present invention extends to a method for treating and/or preventing a physiological state associated with a metabolic syndrome in a patient, comprising administering a therapeutically effective amount of a compound of formula I to the patient.

Furthermore, the present invention extends to a for treating a patient as described above, wherein a therapeutically effective amount of a second active compound for treating and/or preventing the particular disorder or condition is administered.

Moreover, the present invention extends to a pharmaceutical composition comprising a compound of formula I above and a pharmaceutically acceptable carrier.

Accordingly, It is an aspect of the present invention to provide compounds that permit a therapeutically exploitable modulation of the lipid and/or carbohydrate metabolism and are thus suitable for the prevention and/or treatment of disorders such as type 2 diabetes and atherosclerosis and their multifarious sequelae.

This and other aspects of the present invention will be better appreciated by reference to the following Detailed Description.

DETAILED DESCRIPTION OF THE INVENTION

The present invention is based upon the discovery of heretofore unknown compounds that, surprisingly and unexpectedly, are modulators of the activity of peroxisome proliferator-activated receptors (PPARs). Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, $PPARgamma_1$ and $gamma_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 MAY 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Thus broadly, the present invention extends to a compound of the formula I

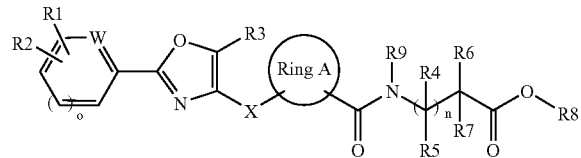

I in which:

Ring A is $(C_3-C_8)$-cycloalkanediyl or $(C_3-C_8)$-cycloalkenediyl, wherein one or more of the carbon atoms of the $(C_3-C8$-cycloalkanediyl or $(C_3-C_8)$ cycloalkenediyl rings may be replaced by oxygen atoms;

R1, R2 are independently of each other H, F, Cl, Br, $CF_3$, $OCF_3$, $(C_1-C_6)$-alkyl, O—$(C_1-C_6)$-alkyl, $SCF_3$, $SF_5$, $OCF_2$—$CHF_2$, $(C_6-C_{10})$-aryl, $(C_6-C_{10})$-aryloxy, OH, $NO_2$; or R1 and R2 together with the phenyl, pyridine, 1H-pyrrole, thiophene or furan ring form fused, partially or unsaturated bicyclic $(C_6-C_{10})$-aryl, $(C_5-C_{11})$-heteroaryl;

R3 is H, $(C_1-C_6)$-alkyl, $(C_3-C_8)$-cycloalkyl, $(C_1-C_3)$-alkyl-$(C_3-C_8)$-cycloalkyl, phenyl, $(C_1-C_3)$-alkyl-phenyl, $(C_5-C_6)$-heteroaryl, $(C_1-C_3)$-alkyl-$(C_5-C_6)$-heteroaryl or $(C_1-C_3)$-alkyl which is fully or partially substituted by F;

W is CH or N if o=1;

W is O, S or NR10 if o=0;

X is $(C_1-C_6)$-alkanediyl, wherein one or more carbon atoms of the $(C_1-C_6)$-alkanediyl group may be replaced by oxygen atoms;

n is 0-2;

R4 is H or $(C_1-C_6)$-alkyl;

R5 is H or $(C_1-C_6)$-alkyl;

R6 is H, $(C_1-C_6)$-alkyl or F;

R7 is H; F; $(C_1-C_6)$-alkoxy; $(C_2-C_6)$-alkenyl; $(C_2-C_6)$-alkynyl; $(C_3-C_8)$-cycloalkyl; phenyl which may be unsubstituted or substituted by one or more radicals from the group consisting of hydroxy, $(C_1-C_6)$-alkoxy, F and $CF_3$; $(C_1-C_6)$-alkyl which may be unsubstituted or substituted by one or more radicals selected from the group consisting of hydroxyl, phenyl, $(C_5-C_{11})$-heteroaryl, $(C_1-C_6)$-alkoxy and NR11R12;

with the proviso that R7 is not NR11R12 or $(C_1-C_6)$-alkoxy if R6=F;

R7 and R9 together with the atoms that carry form pyrrolidine or piperidine if n=0;

R6 and R7 together with the carbon atom that carries them are $(C_3-C_8)$-cycloalkyl;

R8 is H, $(C_1-C_6)$-alkyl;

R9 is H, $(C_1-C_6)$-alkyl, $(C_2-C_6)$-alkenyl, $(C_2-C_6)$-alkynyl, $(C_1-C_4)$-alkyl-$(C_6-C_{10})$-aryl, $(C_1-C_4)$-alkyl-$(C_5-C_{11})$-heteroaryl, $(C_1-C_4)$-alkyl-O—$(C_1-C_4)$-alkyl, phenyl-$(C_1-C_4)$-alkyl, $(C_5-C_6)$-heteroaryl-$(C_1-C_4)$-alkyl;

R10 is H, $(C_1-C_6)$-alkyl-phenyl, $(C_1-C_6)$-alkyl;

R11 is H, $(C_1-C_6)$-alkyl-phenyl, $(C_1-C_6)$-alkyl; and

R12 is H, $(C_1-C_6)$-alkyl-phenyl, $(C_1-C_6)$-alkyl, as well as a physiologically acceptable salt of the compound;

a solvate of the compound; and a physiologically functional derivative of the compound.

Numerous terms and phrases are used throughout the instant specification and Claims. Accordingly:

As used herein, "aryl" refers an aromatic carbocyclic mono- or bicyclic ring system which comprises 6 to 10 atoms in the ring or rings.

As used herein, "heteroaryl" refers to a mono- or bicyclic aromatic ring system having 4 to 11 ring members, in which at least one atom in the ring system is a heteroatom from the series N, O and S.

In addition, a compound of the formula I described above (also referred to as a compound of the present invention or a compound of the invention) comprises at least two centers of asymmetry and may comprise more in addition. The compounds of the formula I may therefore exist in the form of their racemates, racemic mixtures, pure enantiomers, diastereomers and mixtures of diastereomers. The present invention encompasses all these isomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate, likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of the formula I" hereinafter refer to compound(s) of the formula I as described above, and their salts, solvates and physiologically functional derivatives as described herein.

Formulations

As explained above, the present invention extends to a pharmaceutical composition comprising a compound of the present invention, and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human. In particular, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are particular carriers, particularly for injectable solutions. Suitable pharmaceutical carriers are described in "Remington's Pharmaceutical Sciences" by E. W. Martin. Hence, the carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropyl-methylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Methods for Treating and/or Preventing Disease or Condition

This invention relates further to the use of compounds of the formula I and their pharmaceutical compositions as PPAR ligands. The PPAR ligands of the invention are suitable as modulators of PPAR activity. As explained above, PPARs are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

Two variants of PPARgamma exist, PPARgamma$_1$ and gamma$_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 May 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Thus, the present invention extends to a method of treating and/or preventing a disease or condition in a patient, comprising administering a therapeutically effective amount of a compound of formula I to the patient. As used herein, the phrase "therapeutically effective amount" means an amount sufficient to cause an improvement in a clinically significant condition in the patient or even prevent a disease, disorder or condition in a patient. The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of a disease or condition set forth below, a compound of formula I may be used as the compound itself, but they are particularly in the form of a pharmaceutical composition with a pharmaceutically acceptable carrier.

Numerous diseases, disorders or conditions can be treated and/or prevented with a method of the present invention. Particular examples include, but certainly are not limited to:

1.—disorders of fatty acid metabolism and glucose utilization disorders disorders in which insulin resistance is involved Diabetes mellitus, especially type 2 diabetes, including the prevention of the sequelae associated therewith.

Particular aspects in this connection are
hyperglycemia,
improvement in insulin resistance,
improvement in glucose tolerance,
protection of the pancreatic $\beta$ cells
prevention of macro- and microvascular disorders 3. Dyslipidemias and their sequelae such as, for example, atherosclerosis, coronary heart disease, cerebrovascular disorders etc, especially those (but not restricted thereto) which are characterized by one or more of the following factors:

high plasma triglyceride concentrations, high postprandial plasma triglyceride concentrations,
low HDL cholesterol concentrations
low ApoA lipoprotein concentrations
high LDL cholesterol concentrations
small dense LDL cholesterol particles
high ApoB lipoprotein concentrations 4. Various other conditions which may be associated with the metabolic syndrome, such as:

obesity (excess weight), including central obesity thromboses, hypercoagulable and prothrombotic states (arterial and venous)

high blood pressure heart failure such as, for example (but not restricted thereto), following myocardial infarction, hypertensive heart disease or cardiomyopathy 5. Other disorders or conditions in which inflammatory reactions or cell differentiation may for example be involved are:

atherosclerosis such as, for example (but not restricted thereto), coronary sclerosis including angina pectoris or myocardial infarction, stroke vascular restenosis or reocclusion chronic inflammatory bowel diseases such as, for example, Crohn's disease and ulcerative colitis pancreatitis other inflammatory states retinopathy adipose cell tumors lipomatous carcinomas such as, for example, liposarcomas solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc acute and chronic myeloproliferative disorders and lymphomas angiogenesis neurodegenerative disorders Alzheimer's disease multiple sclerosis Parkinson's disease erythemato-squamous dermatoses such as, for example, psoriasis acne vulgaris other skin disorders and dermatological conditions which are modulated by PPAR eczemas and neurodermitis dermatitis such as, for example, seborrheic dermatitis or photodermatitis keratitis and keratoses such as, for example, seborrheic keratoses, senile keratoses, actinic keratosis, photo-induced keratoses or keratosis follicularis keloids and keloid prophylaxis warts, including condylomata or condylomata acuminata human papilloma viral (HPV) infections such as, for example, venereal papillomata, viral warts such as, for example, molluscum contagiosum, leukoplakia papular dermatoses such as, for example, Lichen planus skin cancer such as, for example, basal-cell carcinomas, melanomas or cutaneous T-cell lymphomas localized benign epidermal tumors such as, for example, keratoderma, epidermal naevi chilblains high blood pressure syndrome X polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Combinations with other Medicaments

In a method of the present invention for treating and/or preventing a disease, disorder, or condition in a patient, a compound of the formula I can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www-.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidindiones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin. In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexylmethyl}-amide hydrochloride (CGP 71683A)), MC4 agonists (e.g. 1-amino-1,2,3,4-tetrahydronaphthalene-2-carboxylic acid[2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetra-hydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The present invention may be better understood by reference to the following non-limiting Examples, which are provided as exemplary of the invention. The following Examples are presented in order to more fully illustrate the particular embodiments of the present invention. They should in no way be construed, however, as limiting the broad scope of the invention.

Assays (A) Determination of EC50 Values of PPAR Agonists in the Cellular PPARalpha Assay Principle The potency of substances which bind to human PPAR☐ and activate in an agonistic manner is analyzed using a stably transfected HEK cell line (HEK=human embryo kidney) which is referred to here as PPARalpha reporter cell line. It contains two genetic elements, a luciferase reporter element (pΔM-GAL4-Luc-Zeo) and a PPARalpha fusion protein (GR-GAL4-humanPPARα-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARα ligands bind and activate the PPARα fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CGGAGTACTGTCCTCCGAG-3') (SEQ ID NO:1) were cloned in 5'-upstream of a 68 bp-long minimal MMTV promoter (Genbank Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* gene (Genbank Accession # M15077) was cloned in 3'-downstream of the GAL4-MMTV element. After sequencing, the luceriferase reporter element consisting of five GAL4 binding sites, MMTV promoter and luciferase gene was recloned into a plasmid which confers zeocin resistance in order to obtain the plasmid pΔM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene. In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3'-end of this GR-GAL4 construct. The fusion construct prepared in this way (GR-GAL4-humanP-PARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARα reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% CO2 for 24 h.

Day 3

The PPARα reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL. Fit program as specified by the manufacturer (IDBS).

The PPARalpha EC50 values for the compounds of Examples 1 to 50 in this assay are in the range from 1 nM to >10 µM.

The results for the activity of some compounds of the invention of the formula I are indicated in Table I below:

TABLE 1

| Example No. | EC50 PPARalpha [nM] |
|---|---|
| 3 | 99 |
| 5 | 29 |
| 11 | 15 |
| 21a | 5.0 |
| 25 | 7.2 |
| 43 | 32 |
| 44 | 4.5 |
| 50 | 1.2 |

It is evident from Table I that the compounds of the invention of the formula I activate the PPARalpha receptor and thus bring about for example in analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345-52, 2001; S. Kersten et al.: Roles of PPARs in health and disease, NATURE, VOL 405, 25 May 2000, 421-4; I. Pineda et al.: Peroxisome proliferator-activated receptors: from transcriptional control to clinical practice, Curr Opin Lipidol 12: 2001, 245-254).

(B) Determination of EC50 Values of PPAR Agonists in the Cellular PPARgamma Assay Principle A transient transfection system is employed to determine the cellular PPARgamma activity of PPAR agonists. It is based on the use of a luciferase reporter plasmid (pGL3basic-5×GAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARγ assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5×GAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3') (SEQ ID NO:2), together with a 160 bp-long thymidine kinase promoter section (Genbank Accession # AF027128) 5'-upstream into pGL3basic. 3'-downstream of the thymidine kinase promoter is the complete luciferase gene from *Photinus pyralis* (Genbank Accession # M15077) which is already a constituent of the plasmid pGL3basic used. The cloning and sequencing of the reporter plasmid pGL3basic-5×GAL4-TK took place in analogy to the description in Sambrook J. et. al. (Molecular cloning, Cold Spring Harbor Laboratory Press, 1989).

The PPARgamma expression plasmid pcDNA3-GAL4-humanPPARγLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARγ receptor (amino acids I152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5× GAL4-TK and the PPARγ expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (# 41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (# 41965-039, Invitrogen), 100 µl of reference plasmid pRL-CMV (1 ng/µl), 100 µl of luciferase reporter plasmid pGL3basic-5×GAL4-TK (10 ng/µl), 100 µl of PPARγ expression plasmid pcDNA3-GAL4-humanPPARγLBD (100 ng/µl) and 78 µl of plasmid pBluescript SK(+) (500 ng/µl). Then 2 ml of solution B are prepared by mixing 1.9 ml of DMEM (# 41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min. 80%-confluent HEK cells from a cell culture bottle with a capacity of 175 cm² are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (# 41965-039, Invitrogen) which is mixed with 10% FCS (# 16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µl of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (# 41965-039, Invitrogen) which is mixed with 2% Ultroser (#12039-012, Biosepra),1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM. The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARγ agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 1 nM to >10 µM were measured for the PPAR agonists described in this application.

As explained above, the examples provided below serve to illustrate the invention, but without limiting it.

TABLE II

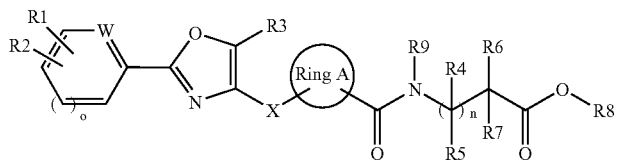

Hereinbelow:
Ring A = cis-cyclohexan-1,3-diyl, with the stereochemistry according to
Cahn-Ingold-Prelog, as specified in the claims; R4 = R5 = H, and R8 = H.

| Ex. | R1 | R2 | R3 | W | X | n | R6 | R7 | R9 |
|---|---|---|---|---|---|---|---|---|---|
| 1 | p-CH3 | H | CH3 | CH | —CH2O— | 0 | H | (S)-i-C3H7 | H |
| 2 | p-CH3 | H | CH3 | CH | —CH2O— | 0 | H | (S)-i-C4H9 | H |
| 3 | p-CH3 | H | CH3 | CH | —CH2O— | 0 | H | (S)—CH3 | H |
| 4 | p-CH3 | H | CH3 | CH | —CH2O— | 0 | H | (S)—PhCH2 | H |
| 5 | p-CH3 | H | CH3 | CH | —CH2O— | 0 | CH3 | CH3 | H |
| 6 | p-CH3 | H | CH3 | CH | —CH2O— | 0 | H | (R)-i-C3H7 | H |
| 7 | m-OCH3 | H | CH3 | CH | —CH2O— | 0 | H | (2S)-pyrrolidin-2-yl | |
| 8 | p-CH3 | H | CH3 | CH | —CH2O— | 0 | H | (2S)-pyrrolidin-2-yl | |
| 9 | m-OCH3 | H | CH3 | CH | —CH2O— | 0 | H | (S)-i-C3H7 | H |
| 10 | m-Br | H | CH3 | CH | —CH2O— | 0 | H | (S)-i-C3H7 | H |
| 11 | m-CF3 | H | CH3 | CH | —CH2O— | 0 | H | (S)-i-C3H7 | H |
| 12 | p-CH3 | H | i-C3H7 | CH | —CH2O— | 0 | H | (S)-i-C3H7 | H |
| 13 | m-OCH3 | H | i-C3H7 | CH | —CH2O— | 0 | H | (S)-i-C3H7 | H |
| 14 | m-OCH3 | H | i-C3H7 | CH | —CH2O— | 0 | H | (S)-i-C3H7 | H |
| 15 | m-OCH3 | H | CF3 | CH | —CH2O— | 0 | H | (S)-i-C3H7 | H |
| 16 | m-CF3 | H | CF3 | CH | —CH2O— | 0 | H | (S)-i-C3H7 | H |
| 17 | p-CH3 | H | CF3 | CH | —CH2O— | 0 | H | (S)-i-C3H7 | H |
| 18 | p-CH3 | H | Ph | CH | —CH2O— | 0 | H | (S)-i-C3H7 | H |
| 19 | m-OCH3 | H | Ph | CH | —CH2O— | 0 | H | (S)-i-C3H7 | H |
| 20 | m-OCH3 | H | Et | CH | —CH2O— | 0 | H | (S)-i-C3H7 | H |
| 21 | p-CH3 | H | Et | CH | —CH2O— | 0 | H | (S)-i-C3H7 | H |
| 22 | m-OCH3 | H | Cy | CH | —CH2O— | 0 | H | (S)-i-C3H7 | H |
| 23 | p-CH3 | H | Cy | CH | —CH2O— | 0 | H | (S)-i-C3H7 | H |
| 24 | p-CH3 | H | CH3 | CH | —CH2O— | 0 | cyclohexyl | | H |
| 25 | p-CH3 | H | CH3 | CH | —CH2O— | 0 | cyclopentyl | | H |
| 26 | m-OCH3 | H | CH3 | CH | —CH2O— | 0 | cyclopentyl | | H |
| 27 | m-CF3 | H | CH3 | CH | —CH2O— | 0 | cyclopentyl | | H |
| 28 | p-CH3 | H | CH3 | CH | —CH2O— | 0 | H | (S)-i-C3H7 | CH3 |
| 29 | p-CH3 | H | CH3 | CH | —CH2O— | 0 | H | (S)-i-C3H7 | PhCH2 |
| 30 | p-CH3 | H | CH3 | CH | —CH2O— | 0 | H | (S)-i-C3H7 | n-C3H7 |
| 31 | p-CH3 | H | C2H5 | CH | —CH2O— | 0 | cyclopentyl | | H |
| 32 | m-OCH3 | m'-OCH3 | CH3 | CH | —CH2O— | 0 | cyclopentyl | | H |
| 33 | m-CF3 | H | i-C3H7 | CH | —CH2O— | 0 | cyclopentyl | | H |
| 34 | m-CF3 | H | C2H5 | CH | —CH2O— | 0 | cyclopentyl | | H |
| 35 | m-CH3 | p-CH3 | i-C3H7 | CH | —CH2O— | 0 | cyclopentyl | | H |
| 36 | p-OCH3 | H | CH3 | CH | —CH2O— | 0 | cyclopentyl | | H |
| 37 | 2-naphthyl | | C2H5 | CH | —CH2O— | 0 | cyclopentyl | | H |
| 38 | m-OCH3 | H | C2H5 | CH | —CH2O— | 0 | cyclopentyl | | H |
| 39 | p-i-C3H7 | H | CH3 | CH | —CH2O— | 0 | cyclopentyl | | H |
| 40 | p-i-C3H7 | H | C2H5 | CH | —CH2O— | 0 | cyclopentyl | | H |
| 41 | p-CH3 | H | CH3 | CH | —CH2OCH2— | 0 | H | (S)-i-C3H7 | H |
| 42 | m-CH3 | p-CH3 | C2H5 | CH | —CH2OCH2— | 0 | H | (S)-i-C3H7 | H |
| 43 | p-CF3 | H | i-C3H7 | CH | —CH2OCH2— | 0 | H | (S)-i-C3H7 | H |
| 44 | m-CF3 | H | CH3 | CH | —CH2OCH2— | 0 | H | (S)-i-C3H7 | H |
| 45 | p-i-C3H7 | H | C2H5 | CH | —CH2OCH2— | 0 | H | (S)-i-C3H7 | H |
| 46 | p-CH3 | H | C2H5 | CH | —CH2OCH2— | 0 | H | (S)-i-C3H7 | H |
| 47 | m-OCH3 | H | Cy | CH | —CH2OCH2— | 0 | H | (S)-i-C3H7 | H |
| 48 | m-OCH3 | H | CH3 | CH | —CH2OCH2— | 0 | H | (S)-i-C3H7 | H |
| 49 | p-i-C3H7 | H | CH3 | CH | —CH2OCH2— | 0 | H | (S)-i-C3H7 | H |
| 50 | p-CF3 | H | C2H5 | CH | —CH2OCH2— | 0 | H | (S)-i-C3H7 | H |

Processes

The compounds of the formula I according to the invention can be obtained according to the reaction schemes below:

Process A:

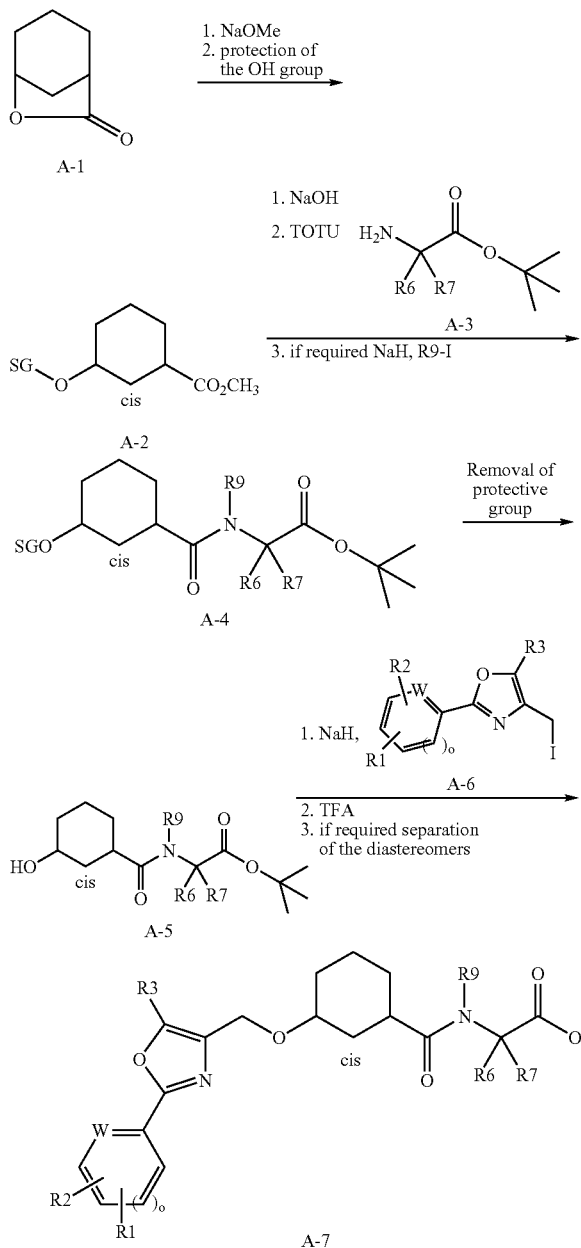

Process B:

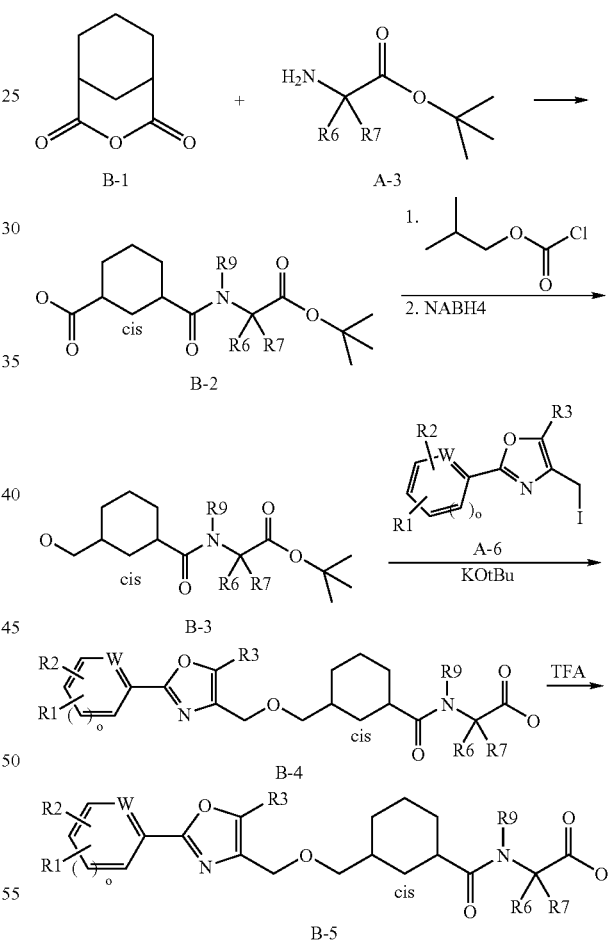

At room temperature, compound A-1 is stirred with sodium methoxide in methanol. After work-up, the product is protected at the hydroxyl group (SG=protective group), for example by reaction with tert-butyidiphenylsilyl chloride and imidazole in dimethylformamide at room temperature or with methoxymethyl chloride, ethyldiisopropylamine in dichloromethane. This gives compound A-2.

Compound A-2 is stirred with sodium hydroxide in isopropanol at 60° C. for 1 hour and worked up. The carboxylic acid obtained in this manner is, in dimethylformamide, reacted with the tert-butyl ester of an α-amino acid of the formula A-3 in which R6 and R7 are as defined above, hydroxybenzotriazole, diisopropylethylamine and O-[cyano(ethoxycarbonyl)methyleneamino]-1,1,3,3-tetramethyluronium tetrafluoroborate (TOTU) to give the product of the formula A-4 in which R9=H. In some examples, the coupling product is reacted with sodium hydride and an alkyl iodide of the formula R9-I where R9 is as defined above, except for R9=H, to give the compound of the formula A-4.

Compound A-4 is then O-deprotected to give compound A-5 using, for example, tetrabutylammonium fluoride in tetrahydrofuran in the case of the tert-butyidiphenylsilyl protective group or using concentrated hydrochloric acid in tetrahydrofuran in the case of the methoxymethyl protective group.

The compound of the formula A-5 is, in dimethylformamide, reacted with sodium hydride and the compound of the formula A-6 in which R1, R2, R3 and W are as defined above. The product is stirred in trifluoroacetic acid for a number of hours and the diastereomers are then, if required, separated by preparative HPLC. This gives the compound of the formula A-7.

According to this process, it is possible to synthesize examples 1 to 40.

At 0° C., the compounds B-1 and an amino acid of the formula A-3 in which R6, R7 and R9 are as defined above are initially charged in dimethyl formamide, and triethylamine and catalytic amounts of dimethylaminopyridine are added. The mixture is stirred at room temperature. After work-up, the product of the formula B-2 is reduced, for example by reaction with isobutyl chloroformate and triethylamine in tetrahydrofuran followed by addition of sodium borohydride to give the compound of the formula B-3 in which R6, R7 and R9 are as defined above. Compound B-3 is converted with potassium tert-butoxide and an alkyl iodide of the formula A-6 in which R1, R2 and R3 are as defined above into the compound of the formula B-4 in which R1, R2, R3, R6, R7 and R9 are as defined above. Compound B-4 is then deprotected, for example by reaction with trifluoroacetic acid in dichloromethane, to give the compound of the formula B-5 in which R1, R2, R3, R6, R7 and R9 are as defined above.

According to this process, it is possible to synthesize examples 41 to 50.

Process C:

This process serves for the synthesis of building block A, where R1, R2, W and R3 are as defined above.

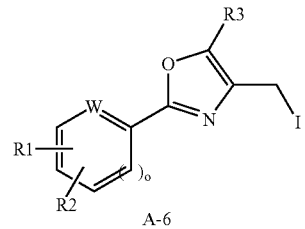

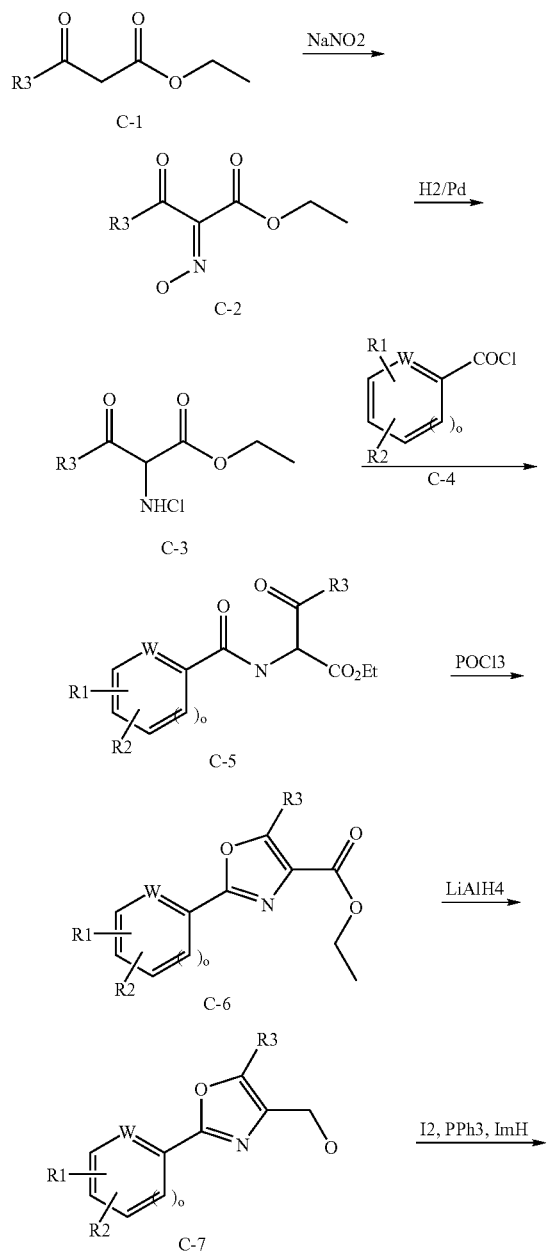

Ester C-1, in which R3 is as defined above, is converted with sodium nitrite and hydrochloric acid into oxime C-2, which is reduced by hydrogenation with hydrogen over palladium/carbon to amine C-3.

The compound C-3 is reacted with acid chlorides of the general formula C-4, in which R1, W and R2 are as defined above, and base (for example triethylamine), to give compound C-5.

Compound C-5 is, by heating in phosphoryl chloride, converted into compound C-6, in which R1, R2, W and R3 are as defined above.

Ester C-6 is reduced with lithium aluminum hydride in an ethereal solvent (e.g. diethyl ether) to alcohol C-7. This is converted (for example with iodine, imidazole (ImH) and triphenylphosphine) into iodide A-6.

Process D:

This process serves for the synthesis of building block A-6, where R1, R2, W and R3 are as defined above.

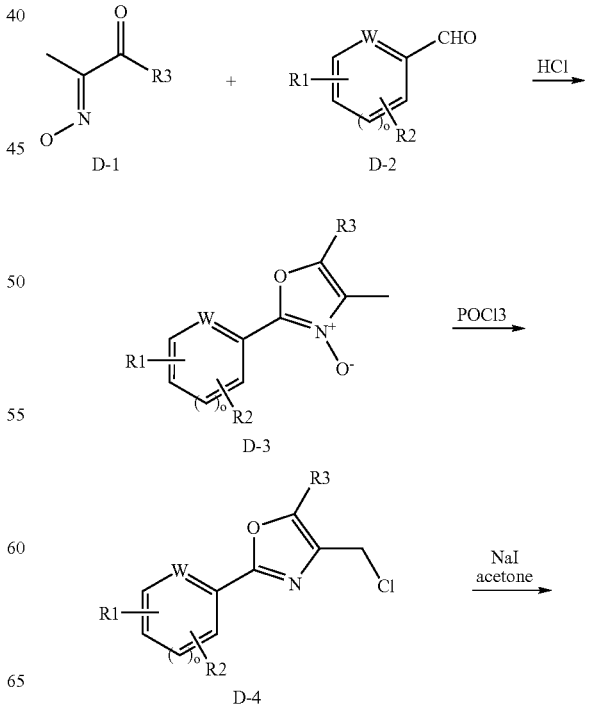

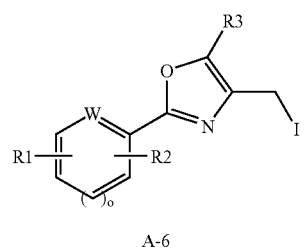

A-6

Compound D-1, in which R3 is as defined above, is reacted with aldehyde D-2, where R1, R2 and W are as defined above, in ethanol with hydrogen chloride, to give compound D-3.

Compound D-3 is, in phosphoryl chloride, heated at the boil, giving compound D-4. This is heated at the boil with sodium iodide in acetone. This gives compound A-6.

Other compounds can be prepared according to the processes mentioned above.

Building block synthesis according to process C:

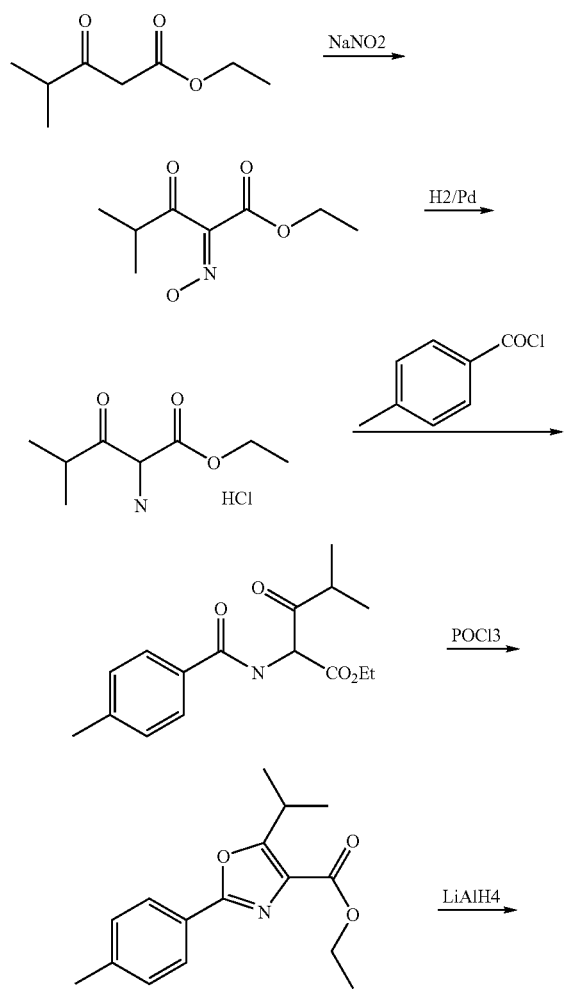

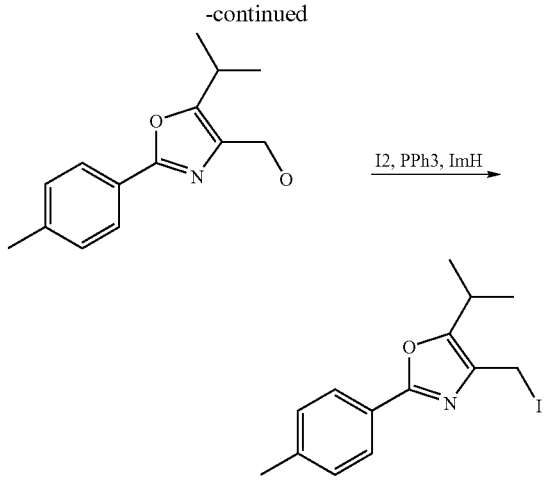

Ethyl 2-hydroxyimino-4-methyl-3-oxopentanoate 42.4 g of ethyl 4-methyl-3-oxopentanoate are dissolved in 100 ml of glacial acetic acid, and 21 g of sodium nitrite, dissolved in 100 ml of water, are added at 5° C. Over a period of one hour, the mixture is allowed to warm to room temperature, 100 ml of water are added and the mixture is stirred at room temperature for another hour. The mixture is extracted three times with in each case 150 ml of methyl tert-butyl ether, 200 ml of water are added to the combined organic phases and the mixture is neutralized by addition of solid NaHCO3. The organic phase is removed, washed with saturated NaCl solution and dried over MgSO4, and the solvent is removed under reduced pressure. This gives 46 g of ethyl 2-hydroxyimino-4-methyl-3-oxopentanoate as an oil. C8H13NO4 (187.20), MS (ESI)=188 (M+H$^+$).

Ethyl 2-amino-4-methyl-3-oxopentanoate hydrochloride

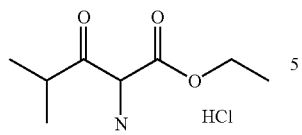

10 g of HCl are introduced into 200 ml of ethanol. 46 g of ethyl 2-hydroxyimino-4-methyl-3-oxopentanoate are dissolved in this mixture, 5 g of Pd (10% on carbon) are added and the mixture is stirred under atmosphere of hydrogen (5 bar) for 8 hours. The reaction mixture is filtered through Celite and the solvent is removed under reduced pressure. This gives 45 g of ethyl 2-amino-4-methyl-3-oxopentanoate hydrochloride as a white solid.

C8H15NO3*HCl (209.5), MS(ESI)=188 (M+H$^+$).

Ethyl 4-methyl-2-(4-methylbenzoylamino)-3-oxopentanoate

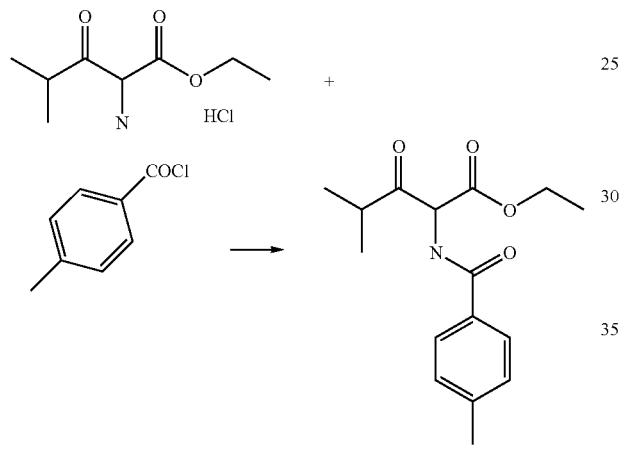

10 g of ethyl 2-amino-4-methyl-3-oxopentanoate hydrochloride and 7.4 g of 4-methylbenzoyl chloride are dissolved in 250 ml of dichloromethane, and 13.3 ml of triethylamine are slowly added dropwise at 0° C. The mixture is stirred at room temperature for one hour and then washed with water, the organic phase is separated off and dried over MgSO4 and the solvent is then removed under reduced pressure. This gives 13 g of ethyl 4-methyl-2-(4-methylbenzoylamino)-3-oxopentanoate as an oil.

C16H21NO4 (291.35), MS(ESI)=292 (M+H$^+$).

Ethyl 5-isopropyl-2-p-tolyloxazole-4-carboxylate

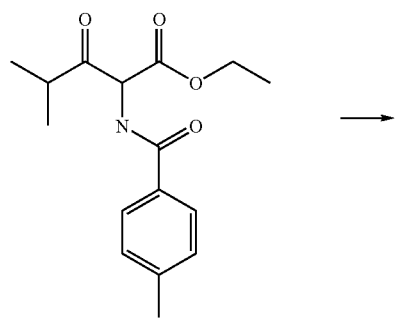

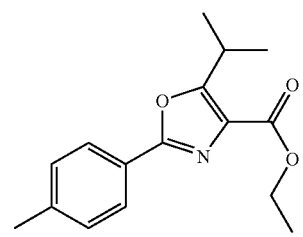

13 g of ethyl 4-methyl-2-(4-methylbenzoylamino)-3-oxopentanoate in 80 ml of phosphorus oxychloride are heated to the boil under reflux for 2 h. The phosphorus oxychloride is removed under reduced pressure and the resulting residue is dissolved in 200 ml of dichloromethane, washed three times with saturated NaHCO$_3$ solution and dried over MgSO4, and the solvent is then removed under reduced pressure. This gives 11 g of ethyl 5-isopropyl-2-p-tolyloxazole-4-carboxylate as a brownish sold. C16H19NO3 (273.33), MS(ESI) =292 (M+H$^+$), Rf(n-heptane:ethyl acetate)=2:1)=0.43.

(5-Isopropyl-2-p-tolyloxazol-4-yl)methanol

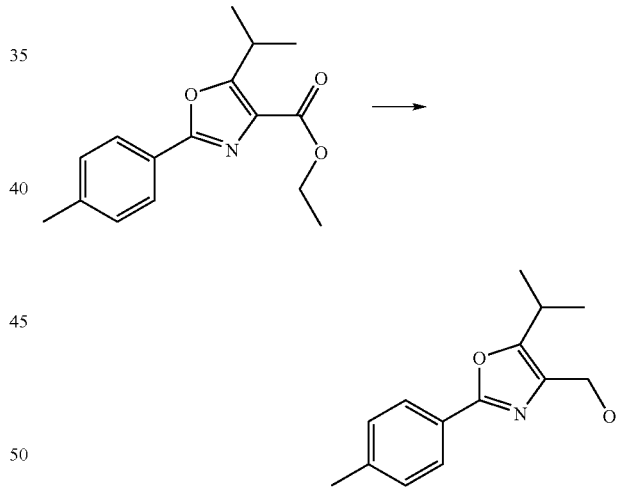

11 g of ethyl 5-isopropyl-2-p-tolyloxazole-4-carboxylate are dissolved in 100 ml of tetrahydrofuran, and 40 ml of a 1 molar solution of lithium aluminum hydride in tetrahydrofuran are added at 0° C. After 30 min, 1N of HCl are added to the reaction mixture, and the mixture is extracted five times with ethyl acetate. The combined organic phases are dried over MgSO4 and the solvent is then removed under reduced pressure. The residue is purified on silica gel using the mobile phase n-heptane:ethyl acetate=6:1=>1:1. This gives 4.3 g of (5-isopropyl-2-p-tolyloxazol-4-yl)methanol as a light-yellow solid.

C14H17NO2 (231.30), MS(ESI)=232 (M+H$^+$), Rf(n-heptane:ethyl acetate)=1:1)=0.17.

4-Iodomethyl-5-isopropyl-2-p-tolyloxazole

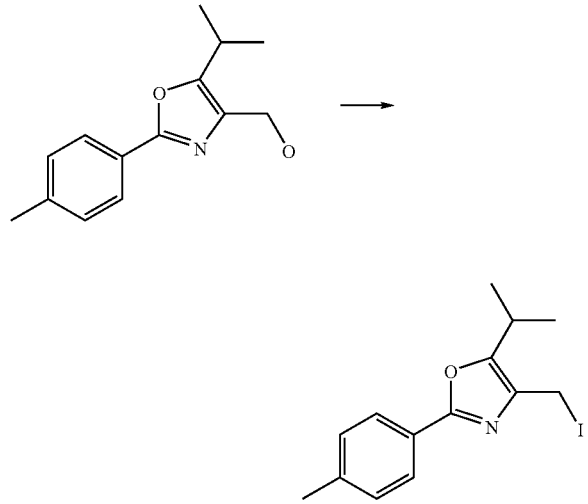

500 mg of (5-isopropyl-2-p-tolyloxazol-4-yl)methanol, together with 690 mg of triphenylphosphine and 600 mg of imidazole, are dissolved in 20 ml of toluene. 715 mg of iodine are added, and the mixture is stirred at room temperature for 1 hour. 10 ml of saturated sodium carbonate solution and 500 mg of iodine are then added. After 10 minutes, the organic phase is separated off, washed twice with saturated Na2S2O3 solution and dried over MgSO4, and the solvents are then removed under reduced pressure. The residue is purified on silica gel using the mobile phase n-heptane:ethyl acetate=10:1. This gives 400 mg of 4-iodomethyl-5-isopropyl-2-p-tolyloxazole as a white solid. C14H16INO (341.19), MS(ESI): 342 (M+H$^+$), Rf(n-heptane:ethyl acetate=1:1)=0.75.

Analogously to the building block synthesis according to process K, ethyl 2-amino-4-methyl-3-oxopentanoate hydrochloride and 3-methoxybenzoyl chloride gave 4-iodomethyl-2-(3-methoxyphenyl)-5-isopropyloxazole.

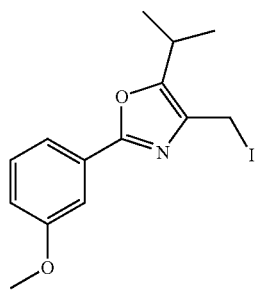

C14H16INO2 (357.19), MS(ESI): 358 (M+H$^+$), Rf(n-heptane:ethyl acetate=1:1)=0.60.

Analogously to the building block synthesis of 4-iodomethyl-5-isopropyl-2-p-tolyloxazole, ethyl 4,4,4-trifluoro-3-oxobutyrate and 3-methoxybenzoyl chloride gave 4-iodomethyl-2-(3-methoxyphenyl)-5-trifluoromethyloxazole.

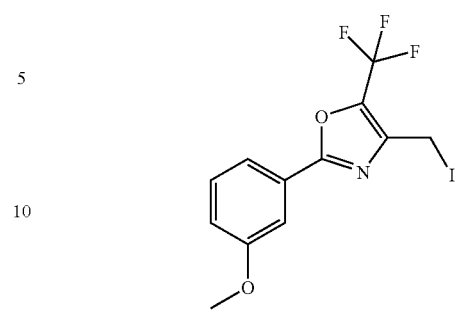

C12H9F3INO2 (383.11), MS(ESI): 384 (M+H$^+$).

Analogously to the building block synthesis of 4-iodomethyl-5-isopropyl-2-p-tolyloxazole, ethyl 4,4,4-trifluoro-3-oxobutyrate and 3-trifluoromethylbenzoyl chloride gave 4-iodomethyl-2-(3-trifluoromethylphenyl)-5-trifluoromethyloxazole.

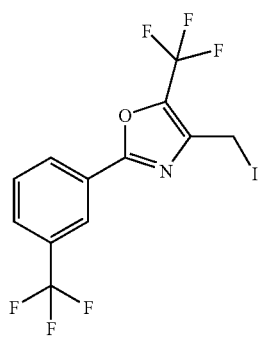

C12H6F6INO (421.08), MS(ESI): 422 (M+H$^+$).

Analogously to the building block synthesis of 4-iodomethyl-5-isopropyl-2-p-tolyloxazole, ethyl 4,4,4-trifluoro-3-oxobutyrate and 4-methylbenzoyl chloride gave 4-iodomethyl-5-trifluoromethyl-2-p-tolyloxazole.

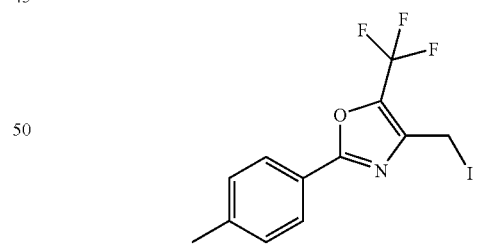

C12H9F3INO (367.11), MS(ESI): 368 (M+H$^+$).

Building Block Synthesis According to Process D:

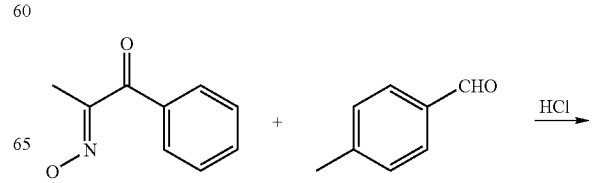

4-Chloromethyl-5-phenyl-2-p-tolyloxazole

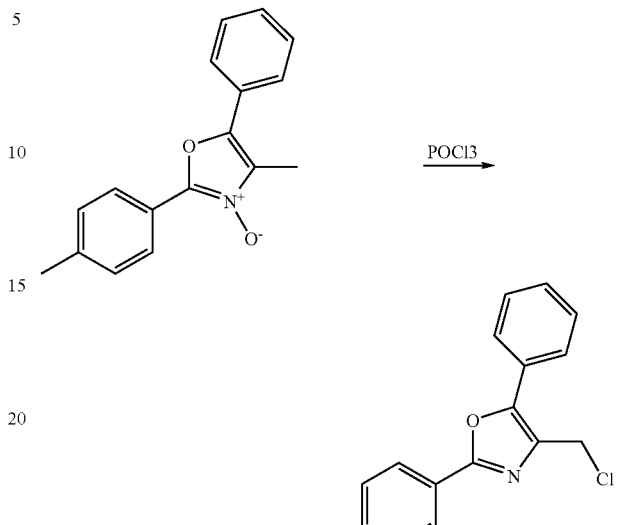

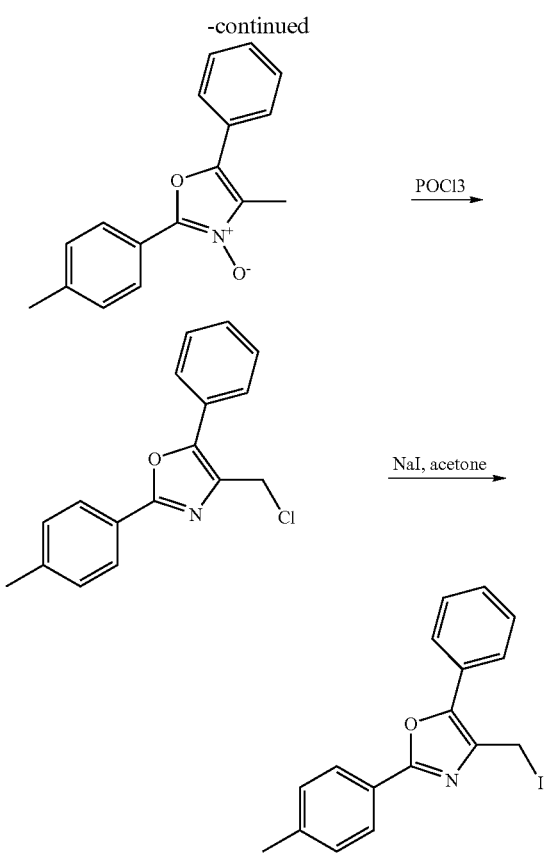

4-Methyl-5-phenyl-2-p-tolyloxazole 3-oxide

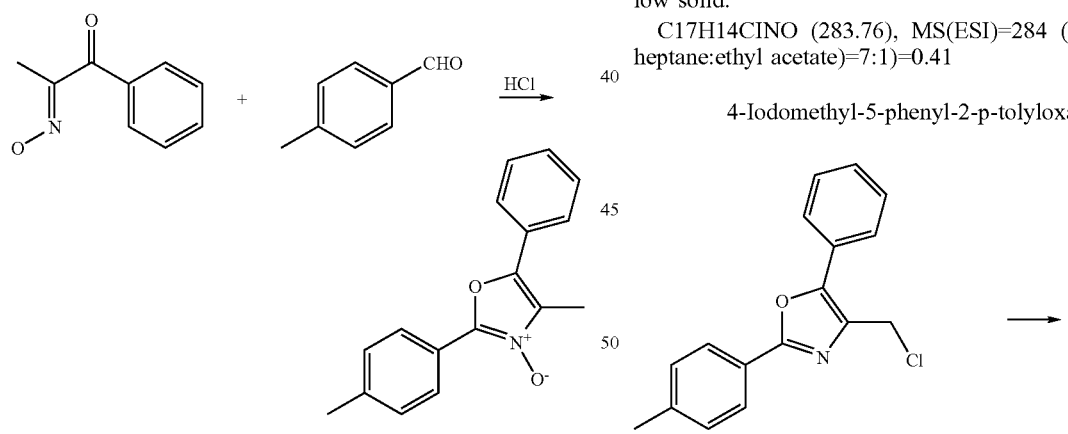

12.5 g of 1-phenyl-1,2-propanedione-2-oxime and 10 ml of p-tolualdehyde are added to 50 ml of glacial acetic acid, and HCl gas is introduced for 30 minutes, with ice-cooling. The product is precipitated as the hydrochloride by addition of methyl tert-butyl ether and filtered off with suction, and the precipitate is washed with methyl tert-butyl ether. The precipitate is suspended in water and the pH is made alkaline using ammonia. The mixture is extracted three times with in each case 200 ml of dichloromethane, the combined organic phases are dried over MgSO4 and the solvent is then removed under reduced pressure. This gives 6.4 g of 4-methyl-5-phenyl-2-p-tolyloxazole 3-oxide as a white solid. C17H15NO2 (265.31), MS(ESI)=266 (M+H+).

6.4 g of 4-methyl-5-phenyl-2-p-tolyloxazole 3-oxide are dissolved in 50 ml of chloroform, 2.4 ml of phosphorus oxychloride are added and the mixture is, under reflux, heated at the boil for 30 minutes. The reaction mixture is cooled to 0° C., the pH is made slightly alkaline using ammonia and the mixture is extracted three times with in each case 100 ml of ethyl acetate. The combined organic phases are washed with water and dried over MgSO4, and the solvent then removed under reduced pressure. This gives 5.4 g of 4-chloromethyl-5-phenyl-2-p-tolyloxazole as a yellow solid.

C17H14ClNO (283.76), MS(ESI)=284 (M+H+), Rf(n-heptane:ethyl acetate)=7:1)=0.41

4-Iodomethyl-5-phenyl-2-p-tolyloxazole

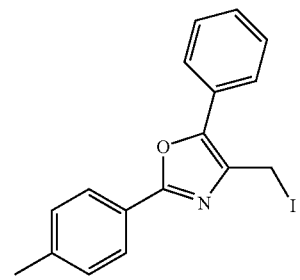

Together with 3 g of sodium iodide, 1.8 g of 4-chloromethyl-5-phenyl-2-p-tolyloxazole are, in 150 ml of acetone, heated at the boil under reflux for 2 hours. After cooling of the reaction mixture, 300 ml of methyl tert-butyl ether are added, the mixture is washed three times with saturated Na2S2O3 solution and dried over MgSO4 and the solvents are then removed under reduced pressure. This gives 2.7 g of 4-iodomethyl-5-phenyl-2-p-tolyloxazole as a light-yellow solid.

C17H14INO (375.21), MS(ESI): 376 (M+H⁺).

Analogously to the building block synthesis of 4-iodomethyl-5-phenyl-2-p-tolyloxazole, 1-phenyl-1,2-propanedione-2-oxime and m-anisaldehyde gave 4-iodomethyl-2-(3-methoxyphenyl)-5-phenyloxazole.

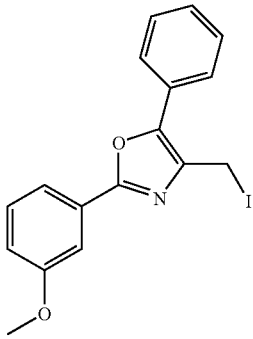

C17H14INO2 (391.21), MS(ESI): 392 (M+H⁺).

Analogously to the building block synthesis of 4-iodomethyl-5-phenyl-2-p-tolyloxazole, 1-ethyl-1,2-propanedione-2-oxime and m-anisaldehyde gave 4-iodomethyl-5-ethyl-2-(3-methoxyphenyl)oxazole.

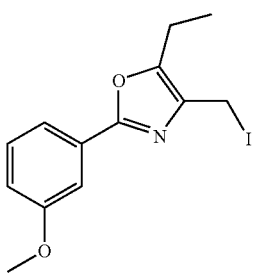

C13H14INO2 (343.17), MS(ESI): 344 (M+H⁺).

Analogously to the building block synthesis of 4-iodomethyl-5-phenyl-2-p-tolyloxazole, 1-ethyl-1,2-propanedione-2-oxime and p-tolualdehyde gave 4-iodomethyl-5-ethyl-2-p-tolylazole.

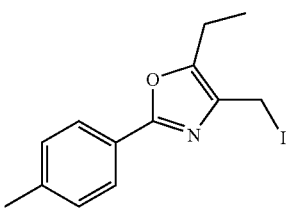

C13H14INO (327.17), MS(ESI): 328 (M+H⁺).

Analogously to the building block synthesis of 4-iodomethyl-5-phenyl-2-p-tolyloxazole, 1-cyclohexyl-1,2-propanedione-2-oxime and m-anisaldehyde gave 4-iodomethyl-5-cyclohexyl-2-(3-methoxyphenyl)oxazole.

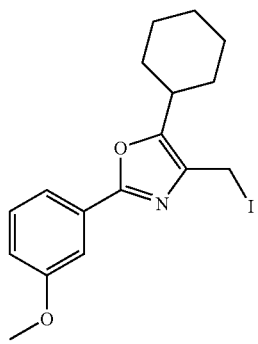

C17H20INO2 (397.26), MS(ESI): 398 (M+H⁺).

Analogously to the building block synthesis of 4-iodomethyl-5-phenyl-2-p-tolyloxazole, 1-cyclohexyl-1,2-propanedione-2-oxime and p-tolualdehyde gave 4-iodomethyl-5-cyclohexyl-2-p-tolyloxazole.

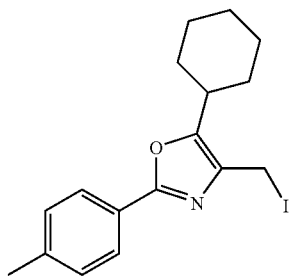

C17H20INO (381.26), MS(ESI): 382 (M+H⁺).

Analogously to the building block synthesis of 4-iodomethyl-5-phenyl-2-p-tolyloxazole, diacetylmonoxime and p-tolualdehyde gave 4-iodomethyl-5-methyl-2-p-tolyloxazole.

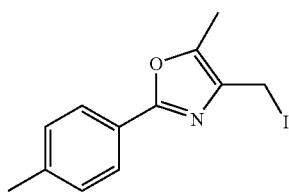

C12H12INO (313.14), MS(ESI): 314 (M+H⁺).

Analogously to the building block synthesis of 4-iodomethyl-5-phenyl-2-p-tolyloxazole, diacetylmonoxime and m-anisaldehyde gave 4-iodomethyl-2-(3-methoxyphenyl)-5-methyloxazole.

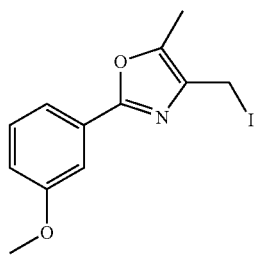

C12H12INO2 (329.14), MS(ESI): 330 (M+H⁺).

Analogously to the building block synthesis of 4-iodomethyl-5-phenyl-2-p-tolyloxazole, diacetylmonoxime and 3-bromobenzaldehyde gave 2-(3-bromophenyl)-4-iodomethyl-5-methyloxazole.

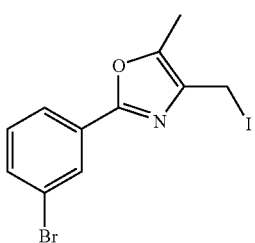

C11H9BrINO (377.01/379.01), MS(ESI): 378/380 (M+H⁺).

Analogously to the building block synthesis of 4-iodomethyl-5-phenyl-2-p-tolyloxazole, diacetylmonoxime and 3-trifluoromethylbenzaldehyde gave 4-iodomethyl-5-methyl-2-(3-trifluoromethylphenyl)oxazole.

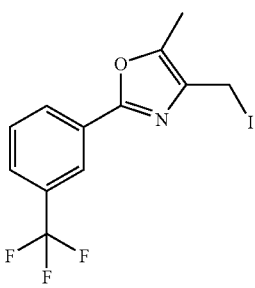

C12H9F3INO (367.11), MS(ESI): 368 (M+H⁺).

Analogously to the building block synthesis of 4-iodomethyl-5-phenyl-2-p-tolyloxazole, diacetylmonoxime and 4-fluorobenzaldehyde gave 2-(4-fluorophenyl)-4-iodomethyl-5-methyloxazole.

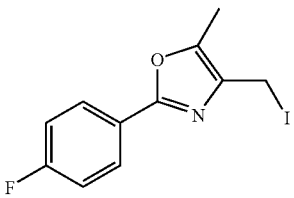

CH11H9FINO (317.10), MS(ESI): 318 (M+H⁺).

Analogously to the building block synthesis of 4-iodomethyl-5-phenyl-2-p-tolyloxazole, diacetylmonoxime and 4-methoxybenzaldehyde gave 4-iodomethyl-2-(4-methoxyphenyl)-5-methyloxazole.

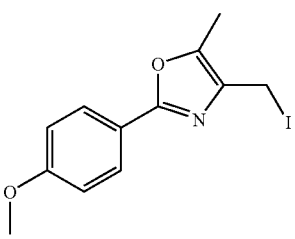

C12H12INO2 (329.14), MS(ESI): 330 (M+H⁺).

Analogously to the building block synthesis of 4-iodomethyl-5-phenyl-2-p-tolyloxazole, diacetylmonoxime and 3-trifluoromethylbenzaldehyde gave 4-iodomethyl-5-methyl-2-(3-trifluoromethylphenyl)-oxazole.

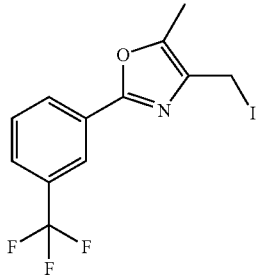

C12H9F3INO (367.11), MS(ESI): 368 (M+H⁺).

Analogously to the building block synthesis of 4-iodomethyl-5-phenyl-2-p-tolyloxazole, diacetylmonoxime and 4-trifluoromethylbenzaldehyde gave 4-iodomethyl-5-methyl-2-(4-trifluoromethylphenyl)oxazole.

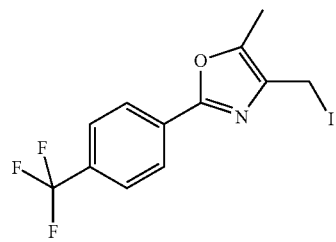

C12H9F3INO (367.11), MS(ESI): 368 (M+H⁺).

Analogously to the building block synthesis of 4-iodomethyl-5-phenyl-2-p-tolyloxazole, diacetylmonoxime and m-tolualdehyde gave 4-iodomethyl-5-methyl-2-m-tolyloxazole.

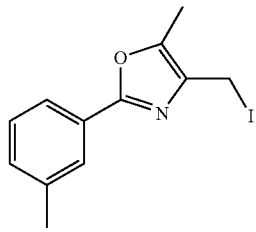

C12H12INO (313.14), MS(ESI): 314 (M+H⁺).

Analogously to the building block synthesis of 4-iodomethyl-5-phenyl-2-p-tolyleoxazole, diacetylmonoxime and 3-trifluoromethoxybenzaldehyde gave 4-iodomethyl-5-methyl-2-(3-trifluoromethoxyphenyl)oxazole.

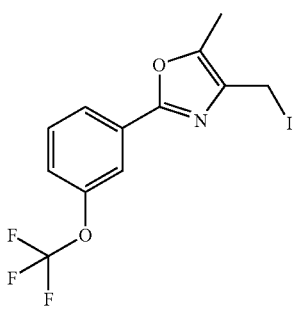

C12H9F3INO2 (383.11), MS(ESI): 384 (M+H⁺).

Analogously to the building block synthesis of 4-ilodomethyl-5-phenyl-2-p-tolyloxazole, diacetylmonoxime and 5-methylfuran-2-carbaldehyde gave 4-iodomethyl-5-methyl-2-(5-methylfuran-2-yl)oxazole.

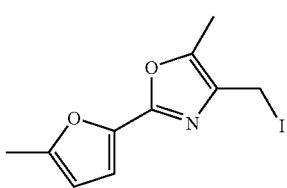

C10H10INO2 (303.11), MS(ESI): 304 (M+H⁺).

Analogously to the building block synthesis of 4-iodomethyl-5-phenyl-2-p-tolyloxazole, diacetylmonoxime and thiophene-2-carbaldehyde gave 4-iodomethyl-5-methyl-2-thiophen-2-yloxazole.

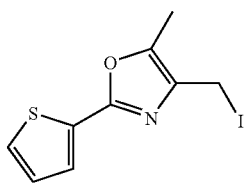

C9H8INOS (305.14), MS(ESI): 306 (M+H⁺).

Analogously to the building block synthesis of 4-iodomethyl-5-phenyl-2-p-tolyloxazole, diacetylmonoxime and 4-isopropylbenzaldehyde gave 4-iodmethyl-2-(4-isopropylphenyl)-5-methyloxazole.

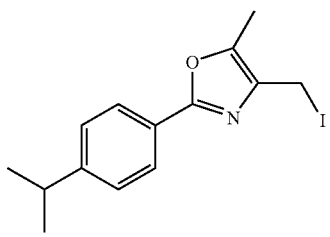

C14H16INO (341.19), MS(ESI): 342 (M+H⁺).

Analogously to the building block synthesis of 4-iodomethyl-5-phenyl-2-p-tolyloxazole, 4-methylpentane-2,3-dione-2-oxime and 3-trifluoromethylbenzaldehyde gave 4-iodomethyl-5-isopropyl-2-(3-trifluoromethylphenyl)-oxazole.

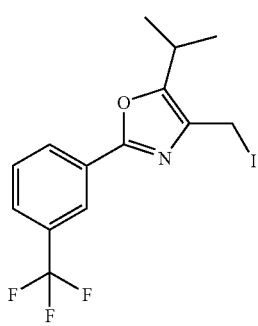

C14H13F3INO (395.17), MS(ESI): 396 (M+H⁺).

Analogously to the building block synthesis of 4-iodomethyl-5-phenyl-2-p-tolyloxazole, pentane-2,3-dione-2-oxime and 3-trifluoromethylbenzaldehyde gave 5-ethyl-4-iodomethyl-2-(3-trifluoromethylphenyl)oxazole.

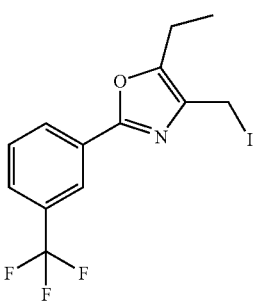

C13H11F3INO (381.14), MS(ESI): 382 (M+H⁺).

Analogously to the building block synthesis of 4-iodomethyl-5-phenyl-2-p-tolyloxazole, 4-methylpentane-2,3-dione-2-oxime and 3,4-dimethylbenzaldehyde gave 2-(3,4-dimethylphenyl)-4-iodomethyl-5-isopropyloxazole.

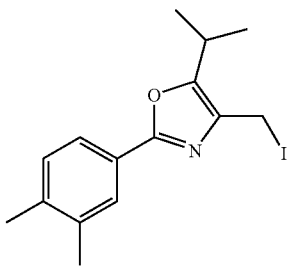

C15H18INO (355.22), MS(ESI): 356 (M+H⁺).

Analogously to the building block synthesis of 4-iodomethyl-5-phenyl-2-p-tolyloxazole, pentane-2,3-dione-2-oxime and naphthalene-2-carbaldehyde gave 5-ethyl-4-iodomethyl-2-naphthalen-2-yloxazole.

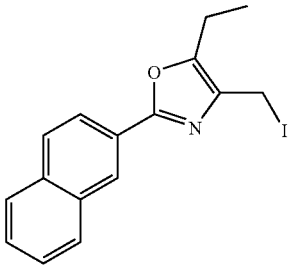

C16H14INO (363.20), MS(ESI): 364 (M+H⁺).

Analogously to the building block synthesis of 4-iodomethyl-5-phenyl-2-p-tolyloxazole, pentane-2,3-dione-2-oxime and 4-isopropylbenzaldehyde gave 5-ethyl-4-iodomethyl-2-(4-isopropylphenyl)oxazole.

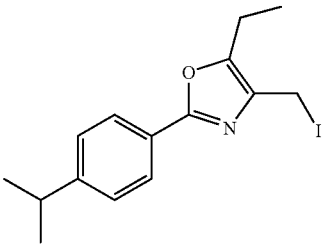

C15H18INO (355.22), MS(ESI): 356 (M+H⁺).

Analogously to the building block synthesis of 4-iodomethyl-5-phenyl-2-p-tolyloxazole, pentane-2,3-dione-2-oxime and 3,4-dimethylbenzaldehyde gave 2-(3,4-dimethylphenyl)-5-ethyl-4-iodomethyloxazole.

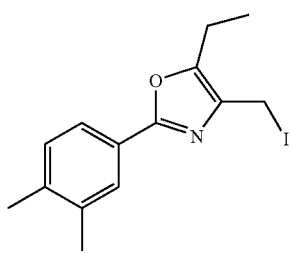
$C_{14}H_{16}INO$ (341.19), MS(ESI): 342 (M+H$^+$).
Analogously to the building block synthesis of 4-iodomethyl-5-phenyl-2-p-tolyloxazole, 4-methylpentane-2,3-dione-2-oxime and 4-trifluoromethylbenzaldehyde gave 4-iodomethyl-5-isopropyl-2-(4-trifluoromethylphenyl)-oxazole.
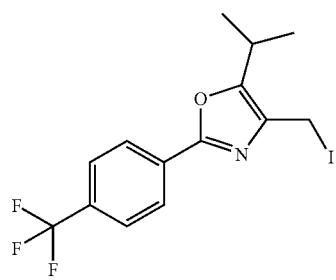
$C_{14}H_{13}F_3INO$ (395.17), MS(ESI): 396 (M+H$^+$).
EXAMPLE 1
(S)-3-Methyl-2-{[(1R,3S)/(1S,3R)-3-(5-methyl-2-p-tolyloxazol-4-ylmethoxy)-cyclohexanecarbonyl]amino}butyric acid
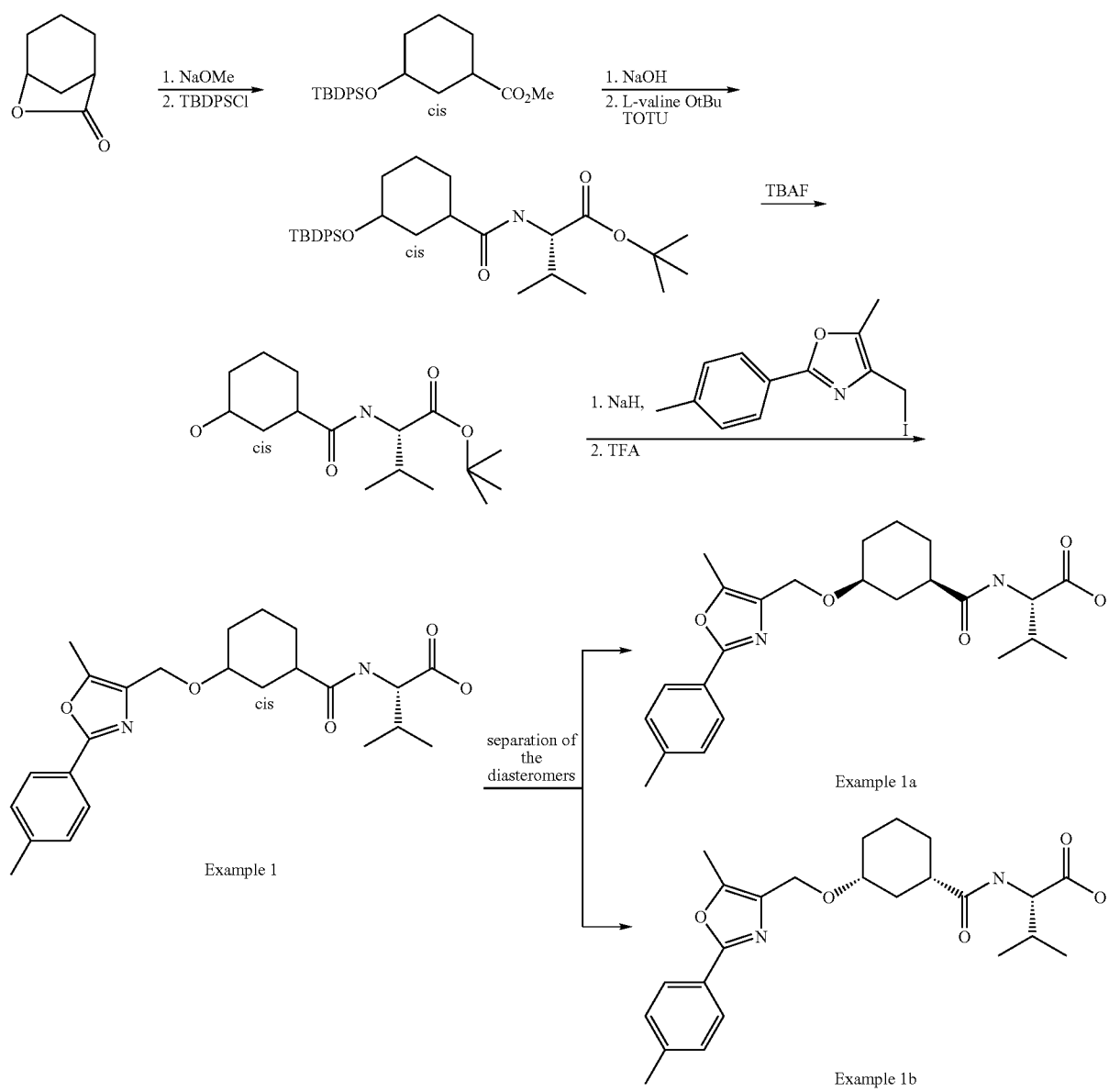

Methyl (1R,3S)/(1S,3R)-3-(tert-butyldiphenylsilanyloxy) cyclohexanecarboxylate

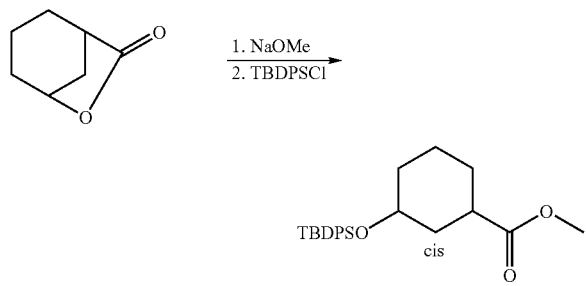

22 g of 6-oxabicyclo[3.2.1]octan-7-one are dissolved in 200 ml of methanol, and 10% strength sodium methoxide solution is added until a pH of 10 is reached. The mixture is stirred at room temperature for 30 minutes and then neutralized by addition of dilute acetic acid, and the mixture is concentrated under reduced pressure. The residue is dissolved in ethyl acetate, dried over MgSO4 and then concentrated under reduced pressure. This gives 21 g of the methyl ester as a colorless oil. This is dissolved in 200 ml of dimethylformamide, 43 g of tert-butyldiphenylsilyl chloride, 13 g of imidazole and 1 g of dimethylaminopyridine are added and the mixture is stirred at room temperature for 12 h. The solvent is removed under reduced pressure and the residue is taken up in methyl tert-butyl ether and washed with water. The organic phase is dried over MgSO4, and the solvent is then removed. This gives 56.8 g of methyl (1R,3S)/(1S,3R)-3-(tert-butyldiphenylsilanyloxy)cyclohexanecarboxylate as a yellow oil. C24H32O3Si (396.61), MS(ESI): 397 (M+H$^+$).

tert-Butyl 2-{[(1R,3S)/(1S,3R)-3-(tert-butyldiphenylsilanyloxy)cyclohexanecarbonyl]amino}-(3S)-methylbutyrate

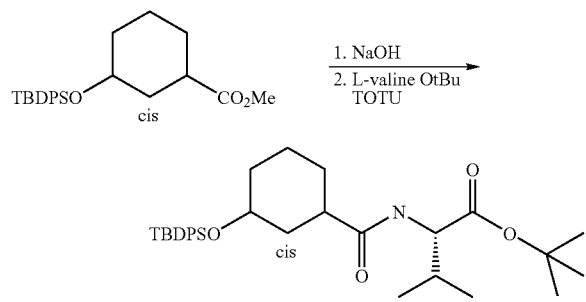

36.8 g of (1R,3S)/(1S,3R)-3-(tert-butyldiphenylsilanyloxy)cyclohexanecarboxylic acid are dissolved in 150 ml of isopropanol, and 8 g of NaOH, dissolved in 50 ml of water, are added. The mixture is heated at 60° C. for 1 hour. The reaction mixture is cooled and neutralized by addition of 2N HCl. The reaction mixture is concentrated under reduced pressure and extracted three times with in each case 200 ml of ethyl acetate. The combined organic phases are dried over MgSO4, and the solvent is then removed under reduced pressure. This gives 34 g of the free acid as a colorless oil (Rf(ethyl acetate)=0.63). This is dissolved in 250 ml of dimethylformamide, and 18.6 g of tert-butyl L-valine hydrochloride are added. At 0° C., 29.1 g of O-[cyano(ethoxycarbonyl)methyleneamino]-1,1,3,3,-tetramethyluronium tetrafluoroborate are added. After 10 minutes, the ice bath is removed, and 23.9 g of hydroxybenzotriazole and 61.8 ml of Hünigs base are added. The mixture is stirred at room temperature for 2 hours. The solvent is removed under reduced pressure and the resulting residue is dissolved in ethyl acetate and washed three times with saturated NaHCO3 solution. The organic phase is dried over MgSO4, and the solvent is then removed. The residue is purified on silica gel using the mobile phase n-heptane:ethyl acetate=2:1. This gives 43.0 g of tert-butyl 2-{[(1R,3S)/(1S,3R)-3-(tert-butyldiphenylsilanyloxy)cyclohexanecarbonyl]-amino}-(3S)-methylbutyrate as a yellow oil.
C32H47NO4Si (537.82), MS(ESI): 538.

tert-Butyl 2-[((1R,3S)/(1S,3R)-3-hydroxycyclohexanecarbonyl)amino]-(3S)-methylbutyrate

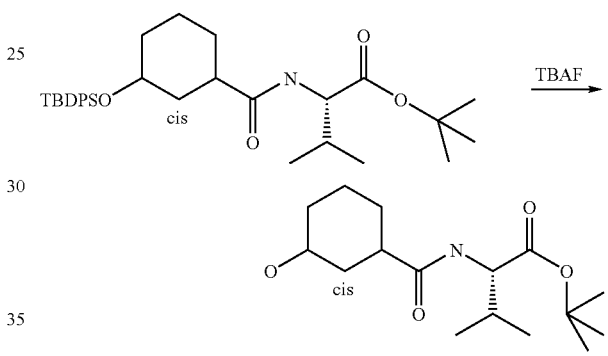

43.0 g of tert-butyl 2-{[(1R,3S)/(1S,3R)-3-(tert-butyldiphenylsilanyloxy)-cyclohexanecarbonyl]amino)-(3S)-methylbutyrate are dissolved in 80 ml of tetrahydrofuran, and 80 ml of a 1 M solution of tetrabutylammonium fluoride in tetrahydrofuran are added. The mixture is stirred at 60° C. for 3 h and then concentrated under reduced pressure, and the residue is purified on silica gel using the mobile phase n-heptane:ethyl acetate=5:1=>1:1. This gives 18 g of a white solid. Since this is still slightly impure, 8 g are subjected to another purification on silica gel. This gives 6.8 g of tert-butyl 2-[((1R,3S)/(1S,3R)-3-hydroxycyclohexanecarbonyl)amino]-3S)-methylbutyrate as a white solid. C16H29NO4 (299.41), MS(ESI): 300 (M+H$^+$).

(S)-3-Methyl-2-{[(1R,3S)/(1S,3R)-3-(5-methyl-2-p-tolyloxazol-4-ylmethoxy)-cyclohexanecarbonyl]amino}butyric acid

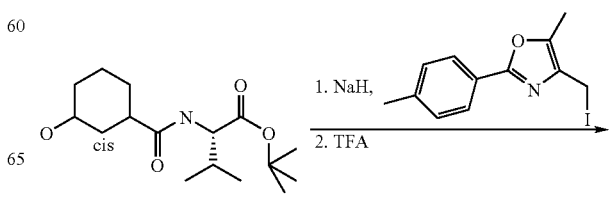

-continued

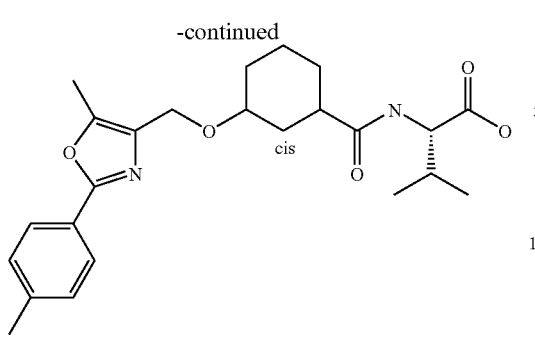

4.0 g of tert-butyl 2-[((1R,3S)/(1S,3R)-3-hydroxycyclohexanecarbonyl)-amino]-(3S)-methylbutyrate and 6.3 g of 4-iodomethyl-5-methyl-2-p-tolyloxazole are dissolved in 50 ml of dimethylformamide, and 800 mg of sodium hydride (60% strength in paraffin oil) are added a little at a time.

The reaction mixture is stirred at room temperature for 1 hour and then diluted by addition of 200 ml of methyl tert-butyl ether and washed three times with water. The combined organic phases are dried over MgSO4, and the solvent is then removed under reduced pressure. The resulting residue is dissolved in 40 ml of dichloromethane, and 20 ml of trifluoroacetic acid are added. The mixture is stirred at room temperature for 5 hours. 100 ml of toluene are then added, and the solvents are removed under reduced pressure. The residue is purified on silica gel using the mobile phase n-heptane:ethyl acetate=2:1=>ethyl acetate. This gives 1.5 g of a brown solid. This is purified further by RP-HPLC. This gives 1.0 g of the diastereomer mixture (S)-3-methyl-2-{[(1R,3S)/(1S,3R)-3-(5-methyl-2-p-tolyloxazol-4-ylmethoxy)cyclohexanecarbonyl]amino)butyric acid (Example 1) as a colorless amorphous solid. C24H32N2O5 (428.53), MS(ESI): 429 (M+H$^+$).

The diastereomer mixture (S)-3-methyl-2-{[(1R,3S)/(1S,3R)-3-(5-methyl-2-p-tolyloxazol-4-ylmethoxy)cyclohexanecarbonyl]amino}butyric acid from Example 1 can be separated by chiral HPLC. This gives (S)-3-methyl-2-{[(1R,3S)-3-(5-methyl-2-p-tolyloxazol-4-ylmethoxy)cyclohexanecarbonyl]-amino}butyric acid (Example 1a) and (S)-3-methyl-2-{[(1S,3R)-3-(5-methyl-2-p-tolyloxazol-4-ylmethoxy)cyclohexanecarbonyl]amino}butyric acid (Example 1b) as colorless lyophilizate. (Chiralpak AD/34 250× 4.6; mobile phase n-heptane:ethanol:methanol=20:1:1+ 0.1% trifluoroacetic acid; (S)-3-methyl-2-{[(1R,3S)-3-(5-methyl-2-p-tolyloxazol-4-ylmethoxy)-cyclohexanecarbonyl]-amino}butyric acid (Example 1a), Rt=4.9 min; (S)-3-methyl-2-{[(1S,3R)-3-(5-methyl-2-p-tolyloxazol-4-ylmethoxy)-cyclohexanecarbonyl]amino}butyric acid (Example 1b), Rt=5.7 min).

EXAMPLE 2

(S)-4-Methyl-2-{[(1R,3S)/(1S,3R)-3-(5-methyl-2-p-tolyloxazol-4-ylmethoxy)-cyclohexanecarbonyl]amino}pentanoic acid Analogously to Example 1, (1R,3S)/(1S,3R)-3-(tert-butyldiphenylsilanyloxy)cyclohexanecarboxylic acid, 4-iodomethyl-5-methyl-2-p-tolyloxazole and tert-butyl (L)-leucine hydrochloride gave the diastereomer mixture (S)-4-methyl-2-{[(1R,3S)/(1S,3R)-3-(5-methyl-2-p-tolyloxazol-4-ylmethoxy)-cyclohexanecarbonyl]amino}pentanoic acid.

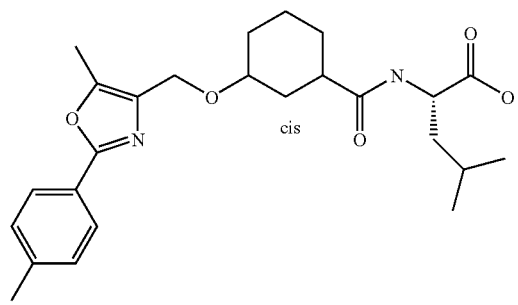

C25H34N2O5 (442.56), MS(ESI): 443 (M+H$^+$).

EXAMPLE 3

(S)-2-{[(1R,3S)/(1S,3R)-3-(5-Methyl-2-p-tolyloxazol-4-ylmethoxy)cyclohexanecarbonyl]amino}propionic acid Analogously to Example 1, (1R,3S)/(1S,3R)-3-(tert-butyldiphenylsilanyloxy)cyclohexanecarboxylic acid, 4-iodomethyl-5-methyl-2-p-tolyloxazole and tert-butyl (L)-alanine hydrochloride gave the diastereomer mixture (S)-2-{[(1R,3S)/(1S,3)-3-(5-methyl-2-p-tolyloxazol-4-ylmethoxy)-cyclohexanecarbonyl]amino}propionic acid.

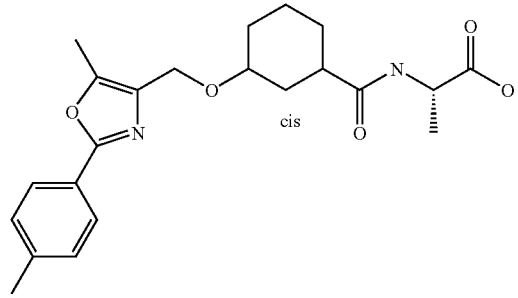

C22H28N2O5 (400.48), MS(ESI): 401 (M+H$^+$).

EXAMPLE 4

(S)-2-}[(1R,3S)/(1S,3R)-3-(5-Methyl-2-p-tolyloxazol-4-ylmethoxy)cyclohexanecarbonyl]amino}-3-phenylpropionic acid Analogously to Example 1, (1R,3S)/(1S,3R)-3-(tert-butyidiphenyl-silanyloxy)cyclohexanecarboxylic acid, 4-iodomethyl-5-methyl-2-p-tolyloxazole and tert-butyl (L)-phenylalaninelanine hydrochloride gave the diastereomer mixture (S)-2-{[(1R,3S)/(1S,3)-3-(5-methyl-2-p-tolyloxazol-4-ylmethoxy)cyclohexanecarbonyl]amino)-3-phenylpropionic acid.

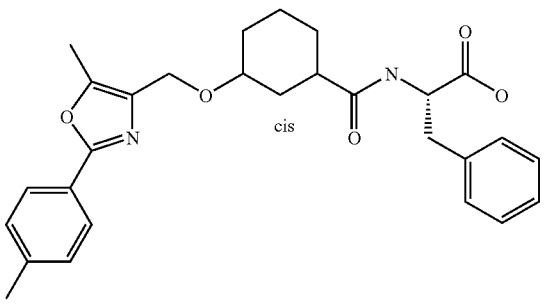

C28H32N2O5 (476.58), MS(ESI): 477 (M+H$^+$).

EXAMPLE 5

2-Methyl-2-{[(1R,3S)/(1S, 3R)-3-(5-methyl-2-p-tolyloxazol-4-ylmethoxy)-cyclohexanecarbonyl]amino}propionic acid Analogously to Example 1, (1R,3S)/(1S,3R)-3-(tert-butyldiphenylsilanyloxy)cyclohexanecarboxylic acid, 4-iodomethyl-5-methyl-2-p-tolyloxazole and tert-butyl 2-amino-2-methylpropionate hydrochloride gave the racemate 2-methyl-2-{[(1R,3S)/(1S,3R)-3-(5-methyl-2-p-tolyloxazol-4-ylmethoxy)cyclohexanecarbonyl]amino}propionic acid.

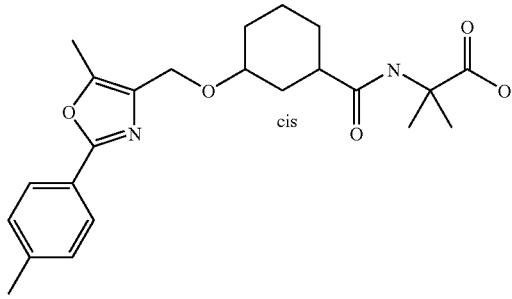

C23H30N2O5 (414.51), MS(ESI): 415 (M+H⁺).

EXAMPLE 6

(R)-3-Methyl-2-{[(1R,3S)/(1S,3R)-3-(5-methyl-2-p-tolyloxazol-4-ylmethoxy)-cyclohexanecarbonyl]amino}butyric acid Analogously to Example 1, (1R,3S)/(1S,3R)-3-(tert-butyldiphenylsilanyloxy)cyclohexanecarboxylic acid, 4-iodomethyl-5-methyl-2-p-tolyloxazole and tert-butyl (D)-valine hydrochloride gave the diastereomer mixture (R)-3-methyl-2-{[(1R,3S)/(1S,3R)-3-(5-methyl-2-p-tolyloxazol-4-ylmethoxy)-cyclohexanecarbonyl]amino}butyric acid.

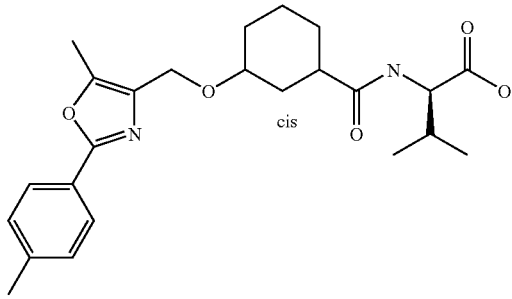

C24H32N2O5 (428.53), MS(ESI): 429 (M+H⁺).

EXAMPLE 7

(S)-1-{(1R,3S)/(1S,3R)-3-[2-(3-Methoxyphenyl)-5-methyloxazol-4-ylmethoxy]cyclohexanecarbonyl}pyrrolidine-2-carboxylic acid Analogously to Example 1, (1R,3S)/(1S,3R)-3-(tert-butyldiphenylsilanyloxy)cyclohexanecarboxylic acid, 4-iodomethyl-2-(3-methoxyphenyl)-5-methyloxazole and tert-butyl (L)-proline hydrochloride gave the diastereomer mixture (S)-1-{(1R,3S)/(1S,3R)-3-[2-(3-methoxyphenyl)-5-methyloxazol-4-ylmethoxy]cyclohexanecarbonyl}pyrrolidine-2-carboxylic acid.

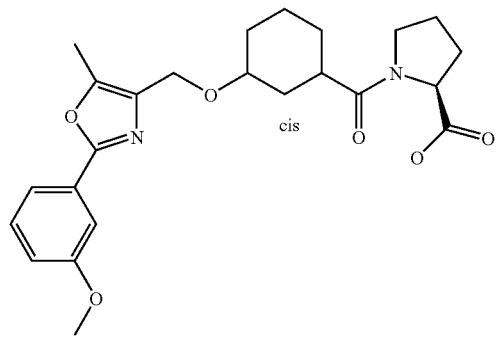

C24H30N2O6 (442.52), MS(ESI): 443 (M+H⁺).

EXAMPLE 8

(S)-1-[(1R,3S)/(1S,3R)-3-(5-Methyl-2-p-tolyloxazol-4-ylmethoxy)-cyclohexanecarbonyl]pyrrolidine-2-carboxylic acid Analogously to Example 1, (1R,3S)/(1S,3R)-3-(tert-butyidiphenylsilanyloxy)cyclohexanecarboxylic acid, 4-iodomethyl-5-methyl-2-p-tolyloxazole and tert-butyl (L)-proline hydrochloride gave the diastereomer mixture (S)-1-[(1R,3S)/(1S,3R)-3-(5-methyl-2-p-tolyloxazol-4-ylmethoxy)cyclohexanecarbonyl]pyrrolidine-2-carboxylic acid.

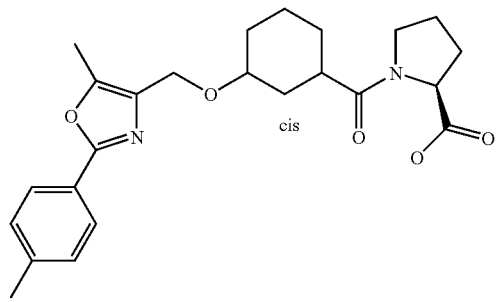

C24H30N2O5 (426.52), MS(ESI): 427 (M+H⁺).

EXAMPLE 9

(S)-2-({(1R,3S)/(1S,3R)-3-[2-(3-Methoxaphenyl)-5-methyloxazol-4-ylmethoxy]cyclohexanecarbonyl}amino)-3-methylbutyric acid Analogously to Example 1, (1R,3S)/(1S,3R)-3-(tert-butyidiphenylsilanyloxy)cyclohexanecarboxylic acid, 4-iodomethyl-2-(3-methoxyphenyl)-5-methyloxazole and tert-butyl (L)-valine hydrochloride gave the diastereomer mixture (S)-2-({(1R,3S)/(1S,3R)-3-[2-(3-methoxyphenyl)-5-methyloxazol-4-ylmethoxy]cyclohexanecarbonyl}amino)-3-methylbutyric acid.

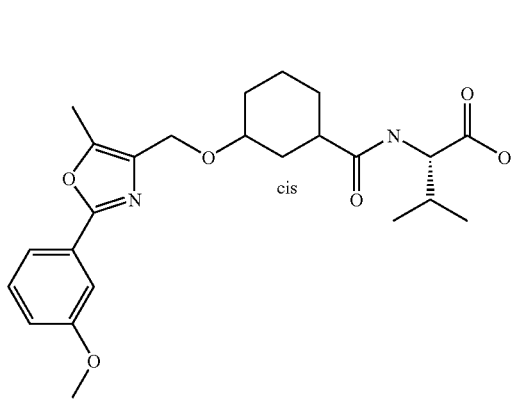

C24H32N2O6 (444.53), MS(ESI): 445 (M+H+).

EXAMPLE 10

(S)-2-({(1R,3S)/(1S,3R)-3-[2-(3-Bromophenyl)-5-methyloxazol-4-ylmethoxy]cyclohexanecarbonyl}amino)-3-methylbutyric acid Analogously to Example 1, (1R,3S)/(1S,3R)-3-(tert-butyldiphenylsilanyloxy)cyclohexanecarboxylic acid, 4-iodomethyl-2-(3-bromophenyl)-5-methyloxazole and tert-butyl (L)-valine hydrochloride gave the diastereomer mixture (S)-2-({(1R,3S)/(1S,3R)-3-[2-(3-bromophenyl)-5-methyloxazol-4-ylmethoxy]cyclohexanecarbonyl}amino-3-methylbutyric acid.

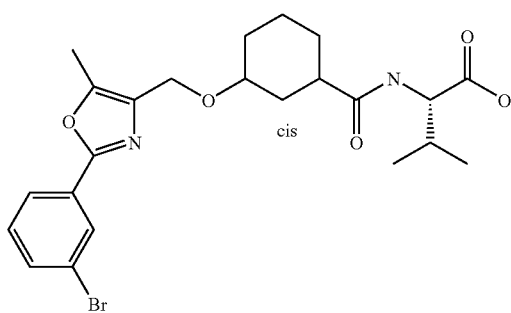

C23H29BrN2O5 (493.40), MS(ESI): 493 (M+H+).

EXAMPLE 11

(S)-3-Methyl-2-({(1R,3S)/(1S,3R)-3-[5-methyl-2-(3-trifluoromethylphenyl)-oxazol-4-ylmethoxy]cyclohexanecarbonyl}amino)butyric acid Analogously to Example 1, (1R,3S)/(1S,3R)-3-(tert-butyldiphenylsilanyloxy)cyclohexanecarboxylic acid, 4-iodomethyl-2-(3-trifluoromethylphenyl)-5-methyloxazole and tert-butyl (L)-valine hydrochloride gave the diastereomer mixture (S)-3-methyl-2-({(1R,3S)/(1S,3R)-3-[5-methyl-2-(3-trifluoromethylphenyl)oxazol-4-ylmethoxy]cyclohexanecarbonyl}-amino)butyric acid.

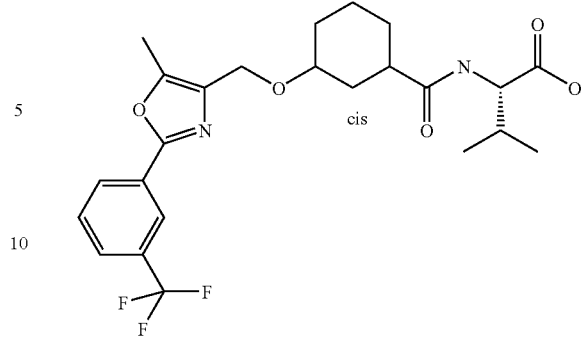

C24H29F3N2O5 (482.50), MS(ESI): 483 (M+H+).

EXAMPLE 12

(S)-2-{[(1R,3S)/(1S,3R)-3-(5-Isopropyl-2-p-tolyloxazol-4-ylmethoxy)-cyclohexanecarbonyl]amino}-3-methylbutyric acid Analogously to Example 1, tert-butyl 2[((1R,3S)/(1S,3R)-3-hydroxy-cyclohexanecarbonyl)amino]-(3S)-methylbutyrate and 4-iodomethyl-2-(4-methylphenyl)-5-isopropyloxazole gave the diastereomer mixture (S)-2-{[(1R,3S)/(1S,3R)-3-(5-isopropyl-2-p-tolyloxazol-4-ylmethoxy)-cyclohexanecarbonyl]amino}-3-methylbutyric acid (Example 12).

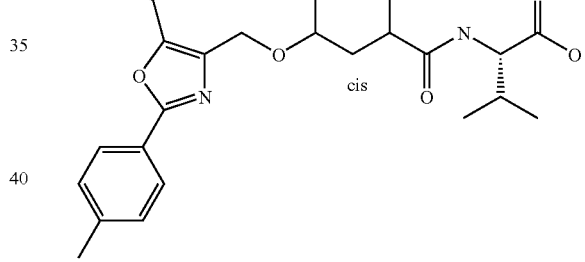

C26H36N2O5 8456.59), MS(ESI): 457 (M+H+).

The diastereomer mixture (S)-2-{[(1R,3S)/(1S,3R)-3-(5-isopropyl-2-p-tolyloxazol-4-ylmethoxy)cyclohexanecarbonyl]amino}-3-methylbutyric acid from Example 12 can be separated by chiral HPLC analogously to Example 1. This gives (S)-2-{[(1R,3S)-3-(5-isopropyl-2-p-tolyloxazol-4-ylmethoxy)cyclohexanecarbonyl]amino}-3-methylbutyric acid (Example 12a) and (S)-2-{[(1S,3R)-3-(5-isopropyl-2-p-tolyloxazol-4-ylmethoxy)cyclohexanecarbonyl]amino}-3-methylbutyric acid (Example 12b) as colorless lyophilizate.

EXAMPLE 13

(S)-2-({(1R,3S)/(1S,3R)-3-[5-Isopropyl-2-(3-methoxyphenyl)oxazol-4-ylmethoxy]cyclohexanecarbonyl}amino)-3-methylbutyric acid Analogously to Example 1, tert-butyl 2-[((1R,3S)/(1S,3R)-3-hydroxycyclohexanecarbonyl}amino]-(3S)-methylbutyrate and 4-iodomethyl-2-(3-methoxyphenyl)-5-isopropyloxazole gave the diastereomer mixture (S)-2-({(1R,3S)/

(1S,3R)-3-[5-isopropyl-2-(3-methoxyphenyl)oxazol-4-ylmethoxy]cyclohexanecarbonyl}amino)-3-methylbutyric acid. (Example 13)

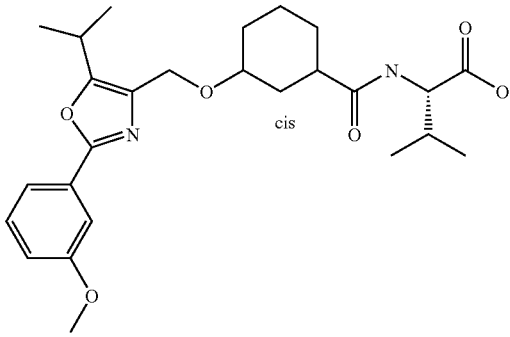

C26H36N2O6 (472.59), MS(ESI): (M+H⁺).

The diastereomer mixture (S)-2-({(1R,3S)/(1S,3R)-3-[5-isopropyl-2-(3-methoxyphenyl)oxazol-4-ylmethoxy]cyclohexanecarbonyl}amino)-3-methylbutyric acid from Example 13 can be separated by chiral HPLC analogously to Example 1. This gives (S)-2-({(1R,3S)-3-[5-isopropyl-2-(3-methoxyphenyl)oxazol-4-ylmethoxy]cyclohexanecarbonyl}amino)-3-methylbutyric acid (Example 13a) and (S)-2-({(1S,3R)-3-[5-isopropyl-2-(3-methoxyphenyl)oxazol-4-ylmethoxy]cyclohexanecarbonyl}amino)-3-methylbutyric acid (Example 13b) as colorless lyophilizate.

EXAMPLE 14

(S)-2-({(1R,3S)/(1S ,3R)-3-[5-Isopropyl-2-(3-methoxyphenyl)oxazol-4-ylmethoxy]cyclohexanecarbonyl}amino)-3-methylbutyric acid Analogously to Example 1, (1R,3S)/(1S,3R)-3-(tert-butyldiphenylsilanyloxy)cyclohexanecarboxylic acid, 4-iodomethyl-2-(3-methoxyphenyl)-5-isopropyloxazole and tert-butyl (L)-valine hydrochloride gave the diastereomer mixture (S)-2-({(1R,3S)/(1S,3R)-3-[5-isopropyl-2-(3-methoxyphenyl)oxazol-4-ylmethoxy]cyclohexanecarbonyl}amino)-3-methylbutyric acid.

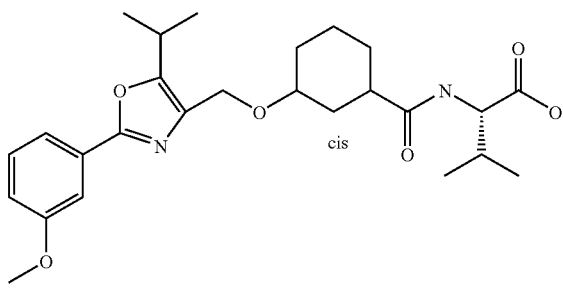

C26H36N2O6 (472.59), MS(ESI): 473 (M+H⁺).

EXAMPLE 15

(S)-2-({(1R,3S)/(1S,3R)-3-[2-(3-Methoxyphenyl)-5-trifluoromethyloxazol-4-ylmethoxy]cyclohexanecarbonyl}amino)-3-methylbutyric acid Analogously to Example 1, tert-butyl 2-[((1R,3S)/(1S,3R)-3-hydroxycyclohexanecarbonyl)amino]-(3S)-methylbutyrate and 4-iodomethyl-2-(3-methoxyphenyl)-5-trifluoromethyloxazole gave the diastereomer mixture (S)-2-({(1R,3S)-3-[2-(3-methoxyphenyl)-5-trifluoromethyloxazol-4-ylmethoxy]cyclohexanecarbonyl}amino)-3-methylbutyric acid.

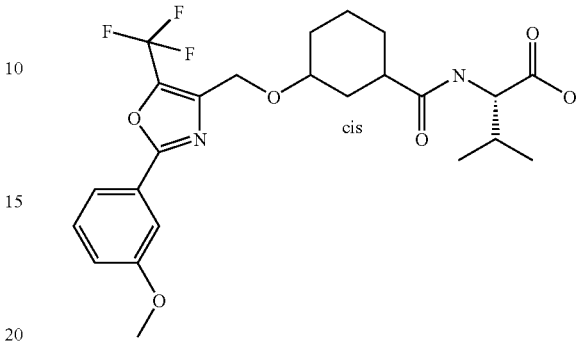

C24H29F3N2O6 (498.50), MS(ESI): 499 (M+H⁺).

The diastereomer mixture (S)-2-({(1R,3S)/(1S,3R)-3-[2-(3-methoxyphenyl)-5-trifluoromethyloxazol-4-ylmethoxy]cyclohexanecarbonyl}amino)-3-methylbutyric acid from Example 15 can be separated by chiral HPLC analogously to Example 1. This gives (S)-2-({(1R,3S)-3-[2-(3-methoxyphenyl)-5-trifluoromethyloxazol-4-ylmethoxy]cyclohexanecarbonyl}amino)-3-methylbutyric acid (Example 15a) and (S)-2-({(1S,3R)-3-[2-(3-methoxyphenyl)-5-trifluoromethyloxazol-4-ylmethoxy]cyclohexanecarbonyl}amino)-3-methylbutyric acid (Example 15b) as colorless lyophilizate.

EXAMPLE 16

(S)-3-Methyl-2-({(1R,3S)/(1S,3R)-3-[5-trifluoromethyl-2-(3-trifluoromethylphenyl)oxazol-4-ylmethoxy]cyclohexanecarbonyl}amino)butyric acid Analogously to Example 1, tert-butyl 2-[((1R,3S)/(1S,3R)-3-hydroxycyclohexanecarbonyl)amino]-(3S)-methylbutyrate and 4-iodomethyl-2-(3-trifluoromethylphenyl)-5-trifluoromethyloxazole gave the diastereomer mixture (S)-3-methyl-2-({(1R,3S)/(1S,3R)-3-[5-trifluoromethyl-2-(3-trifluoromethylphenyl)oxazol-4-ylmethoxy]cyclohexanecarbonyl}amino)butyric acid.

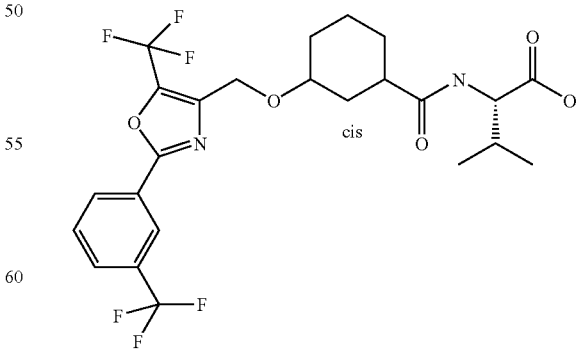

C24H26F6N2O5 (536.48), MS(ESI): 537 (M+H⁺).

The diastereomer mixture (S)-3-methyl-2-({(1R,3S)/(1S,3R)-3-[5-trifluoromethyl-2-(3-trifluoromethylphenyl)oxazol-4-ylmethoxy]cyclohexanecarbonyl}amino)butyric acid from Example 16 can be separated by chiral HPLC analogously to Example 1. This gives (S)-3-methyl-2-({(1R,3S)-3-[5-trifluoromethyl-2-(3-trifluoromethylphenyl)oxazol-4-ylmethoxy]-cyclohexanecarbonyl}amino)butyric acid (Example 16a) and (S)-3-methyl-2-({(1S,3R)-3-[5-trifluoromethyl-2-(3-trifluoromethylphenyl)oxazol-4-ylmethoxy]cyclohexanecarbonyl}amino)butyric acid (Example 16b) as colorless lyophilizate.

EXAMPLE 17

(S)-3-Methyl-2-{[(1R,3S)/(1S,3R)-3-(2-p-tolyl-5-trifluoromethyloxazol-4-ylmethoxy)cyclohexanecarbonyl]amino}butyric acid Analogously to Example 1, tert-butyl 2-[((1R,3S)/(1S,3R)-3-hydroxycyclohexanecarbonyl)amino]-(3S)-methylbutyrate and 4-iodomethyl-2-(4-methyl-phenyl)-5-trifluoromethyloxazole gave the diastereomer mixture (S)-3-methyl-2-{[(1R,3S)/(1S,3R)-3-(2-p-tolyl-5-trifluoromethyloxazol-4-ylmethoxy)cyclohexanecarbonyl]amino}butyric acid.

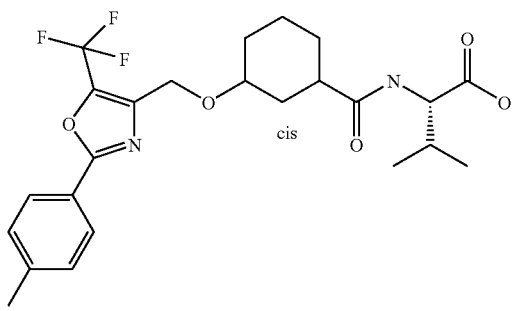

C24H29F3N2O5 (482.50), MS(ESI): 483 (M+H$^+$).

The diastereomer mixture (S)-3-methyl-2-{[(1R,3S)/(1S,3R)-3-(2-p-tolyl-5-trifluoromethyloxazol-4-ylmethoxy)cyclohexanecarbonyl]amino}butyric acid from Example 17 can be separated by chiral HPLC analogously to Example 1. This gives (S)-3-methyl-2-{[(1R,3S)-3-(2-p-tolyl-5-trifluoromethyloxazol-4-ylmethoxy)cyclohexanecarbonyl]amino}butyric acid (Example 17a) and (S)-3-methyl-2-{[(1S,3R)-3-(2-p-tolyl-5-trifluoromethyloxazol-4-ylmethoxy)cyclohexanecarbonyl]amino}butyric acid (Example 17b) as colorless lyophilizate.

EXAMPLE 18

(S)-3-Methyl-2-{[(1R,3S)/(1S,3R)-3-(5-phenyl-2-p-tolyloxazol-4-ylmethoxy)cyclohexanecarbonyl]amino}butyric acid Analogously to Example 1, tert-butyl 2-[((1R,3S)/(1S,3R)-3-hydroxycyclohexanecarbonyl)amino]-(3S)-methylbutyrate and 4-iodomethyl-2-(4-methylphenyl)-5-phenyloxazole gave the diastereomer mixture (S)-3-methyl-2-{[(1R,3S)/(1S,3R)-3-(5-phenyl-2-p-tolyloxazol-4-ylmethoxy)cyclohexanecarbonyl]amino}butyric acid.

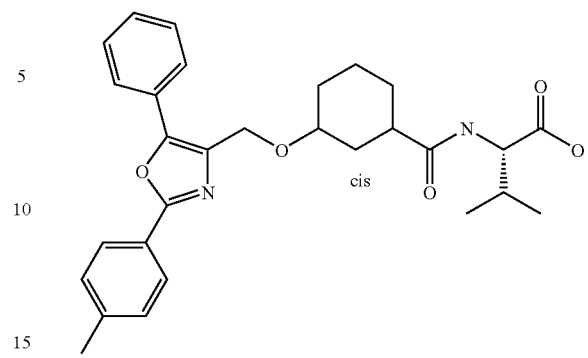

C29H34N2O5 (490.60), MS(ESI): 491 (M+H$^+$).

The diastereomer mixture (S)-3-methyl-2-{[(1R,3S)/(1S,3R)-3-(5-phenyl-2-p-tolyloxazol-4-ylmethoxy)cyclohexanecarbonyl]amino}butyric acid from Example 18 can be separated by chiral HPLC analogously to Example 1. This gives (S)-3-methyl-2-{[(1R,3S)-3-(5-phenyl-2-p-tolyloxazol-4-ylmethoxy)cyclohexanecarbonyl]amino}butyric acid (Example 18a) and (S)-3-methyl-2-{[(1S,3R)-3-(5-phenyl-2-p-tolyloxazol-4-ylmethoxy)cyclohexanecarbonyl]amino}butyric acid (Example 18b) as colorless lyophilizate.

EXAMPLE 19

(S)-2-({(1R,3S)/(1S,3R)-3-[2-(3-Methoxyphenyl)-5-phenyloxazol-4-ylmethoxy]cyclohexanecarbonyl}amino)-3-methylbutyric acid Analogously to Example 1, (1R,3S)/(1S,3R)-3-(tert-butyldiphenylsilanyloxy)cyclohexanecarboxylic acid, 4-iodomethyl-2-(3-methoxyphenyl)-5-phenyloxazole and tert-butyl (L)-valine hydrochloride gave the diastereomer mixture (S)-2-({(1R,3S)/(1S,3R)-3-[2-(3-methoxyphenyl)-5-phenyloxazol-4-ylmethoxy]cyclohexanecarbonyl}amino)-3-methylbutyric acid.

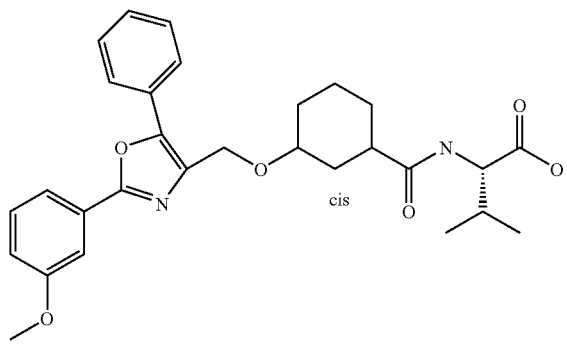

C29H34N2O6 (506.60), MS(ESI): 507 (M+H$^+$).

EXAMPLE 20

(S)-2-({(1R,3S)/(1S,3R)-3-[2-(3-Methoxyphenyl)-5-ethyloxazol-4-ylmethoxy]cyclohexanecarbonyl}amino)-3-methylbutyric acid Analogously to Example 1, tert-butyl 2-[((1R,3S)/(1S,3R)-3-hydroxycyclohexanecarbonyl)amino]-(3S)-methylbutyrate and 4-iodomethyl-2-(3-methoxyphenyl)-5-ethyloxazole gave the diastereomer mixture (S)-2-({(1R,3S)/(1S,3R)-3-[2-(3-methoxyphenyl)-5-ethyloxazol-4-ylmethoxy]cyclohexanecarbonyl}amino)-3-methylbutyric acid.

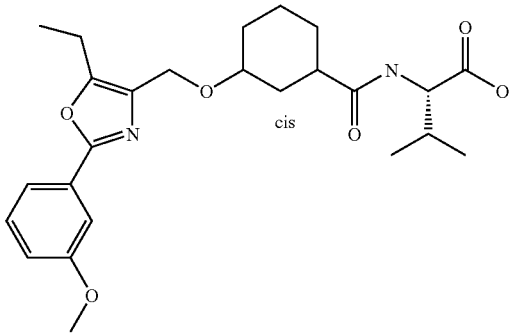

C25H34N2O6 (458.56), MS(ESI): 459 (M+H+).

The diastereomer mixture (S)-2-({(1R,3S)/(1S,3R)-3-[2-(3-methoxyphenyl)-5-ethyloxazol-4-ylmethoxy]cyclohexanecarbonyl}amino)-3-methylbutyric acid from Example 20 can be separated by chiral HPLC analogously to Example 1. This gives (S)-2-({(1R,3S)-3-[2-(3-methoxyphenyl)-5-ethyloxazol-4-ylmethoxy]cyclohexanecarbonyl}amino)-3-methylbutyric acid (Example 20a) and (S)-2-({(1S,3R)-3-[2-(3-methoxyphenyl)-5-ethyloxazol-4-ylmethoxy]cyclohexanecarbonyl}amino)-3-methylbutyric acid (Example 20b) as colorless lyophilizate.

EXAMPLE 21

(S)-3-Methyl-2-{[(1R,3S)/(1S,3R)-3-(5-ethyl-2-p-tolyloxazol-4-ylmethoxy)-cyclohexanecarbonyl]amino}butyric acid Analogously to Example 1, tert-butyl 2-[((1R,3S)/(1S,3R)-3-hydroxycyclohexanecarbonyl)amino]-(3S)-methylbutyrate 4a and 4-iodomethyl-2-(4-methylphenyl)-5-ethyloxazole gave the diastereomer mixture (S)-3-methyl-2-{[(1R,3S)/(1S,3R)-3-(5-ethyl-2-p-tolyloxazol-4-ylmethoxy)cyclohexanecarbonyl]amino}butyric acid.

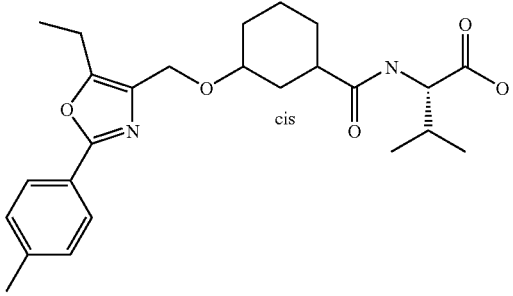

C25H34N2O5 (442.56), MS(ESI): 443 (M+H+).

The diastereomer mixture (S)-3-methyl-2-{[(1R,3S)/(1S,3R)-3-(5-ethyl-2-p-tolyloxazol-4-ylmethoxy)cyclohexanecarbonyl]amino}butyric acid from Example 21 can be separated by chiral HPLC analogously to Example 1. This gives (S)-3-methyl-2-{[(1R,3S)-3-(5-ethyl-2-p-tolyloxazol-4-ylmethoxy)cyclohexanecarbonyl]amino}butyric acid (Example 21a) and (S)-3-methyl-2-{[(1S,3R)-3-(5-ethyl-2-p-tolyloxazol-4-ylmethoxy)cyclohexanecarbonyl]amino}butyric acid (Example 21b) as colorless lyophilizate.

EXAMPLE 22

(S)-2-({(1R,3S)/(1S,3R)-3-[2-(3-Methoxyphenyl)-5-cyclohexyloxazol-4-ylmethoxy]cyclohexanecarbonyl}amino)-3-methylbutyric acid Analogously to Example 1, tert-butyl 2-[((1R,3S)/(1S,3R)-3-hydroxycyclohexanecarbonyl)amino]-(3S)-methylbutyrate and 4-iodomethyl-2-(3-methoxyphenyl)-5-cyclohexyloxazole gave the diastereomer mixture (S)-2-({(1R,3S)/(1S,3R)-3-[2-(3-methoxyphenyl)-5-cyclohexyloxazol-4-ylmethoxy]cyclohexanecarbonyl}amino)-3-methylbutyric acid.

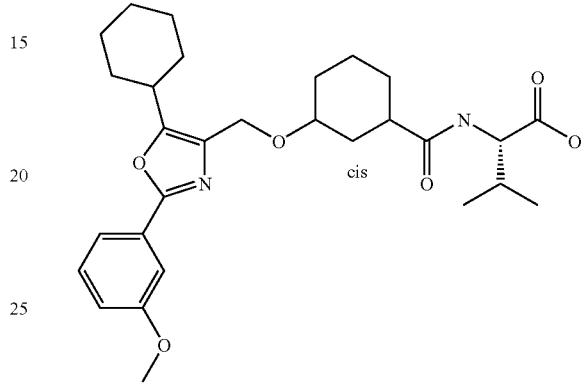

C29H40N2O6 (512.65), MS(ESI): 513 (M+H+).

The diastereomer mixture (S)-2-({(1R,3S)/(1S,3R)-3-[2-(3-methoxyphenyl)-5-cyclohexyloxazol-4-ylmethoxy]cyclohexanecarbonyl}amino)-3-methylbutyric acid from Example 22 can be separated by chiral HPLC analogously to Example 1. This gives (S)-2-({(1R,3S)-3-[2-(3-methoxyphenyl)-5-cyclohexyloxazol-4-ylmethoxy]cyclohexanecarbonyl}amino)-3-methylbutyric acid (Example 22a) and (S)-2-({(1S,3R)-3-[2-(3-methoxyphenyl)-5-cyclohexyloxazol-4-ylmethoxy]cyclohexanecarbonyl}amino)-3-methylbutyric acid (Example 22b) as colorless lyophilizate.

EXAMPLE 23

(S)-3-Methyl-2-{[(1R,3S)/(1S,3R)-3-(5-cyclohexyl-2-p-tolyloxazol-4-ylmethoxy)cyclohexanecarbonyl]amino}butyric acid Analogously to Example 1, tert-butyl 2-[((1R,3S)/(1S,3R)-3-hydroxycyclohexanecarbonyl)amino]-(3S)-methylbutyrate and 4-iodomethyl-2-(4-methylphenyl)-5-cyclohexyloxazole gave the diastereomer mixture (S)-3-methyl-2-{[(1R,3S)/(1S,3R)-3-(5-cyclohexyl-2-p-tolyloxazol-4-ylmethoxy)cyclohexanecarbonyl]amino}butyric acid.

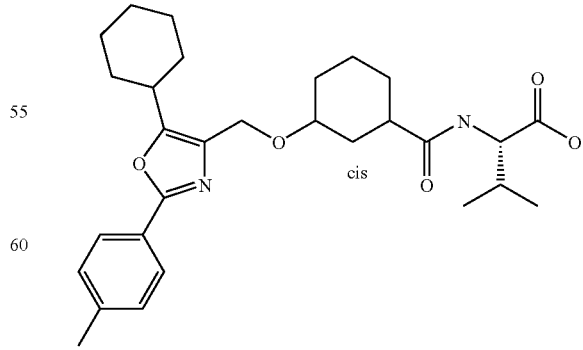

C29H40N2O5 (496.65), MS(ESI): 497 (M+H+).

The diastereomer mixture (S)-3-methyl-2-{[(1R,3S)/(1S,3R)-3-(5-cyclohexyl-2-p-tolyloxazol-4-ylmethoxy)cyclohexanecarbonyl]amino}butyric acid from Example 23 can be separated by chiral HPLC analogously to Example 1. This gives (S)-3-methyl-2-{[(1R,3S)-3-(5-cyclohexyl-2-p-tolyloxazol-4-ylmethoxy)cyclohexanecarbonyl]amino}butyric acid (Example 23a) and (S)-3-methyl-2-{[(1S,3R)-3-(5-cyclohexyl-2-p-tolyloxazol-4-ylmethoxy)cyclohexanecarbonyl]amino}butyric acid (Example 23b) as colorless lyophilizate.

EXAMPLE 24

1-{[(1R,3S)/(1S,3R)-3-(5-Methyl-2-p-tolyloxazol-4-ylmethoxy)cyclohexanecarbonyl]amino}cyclohexanecarboxylic acid

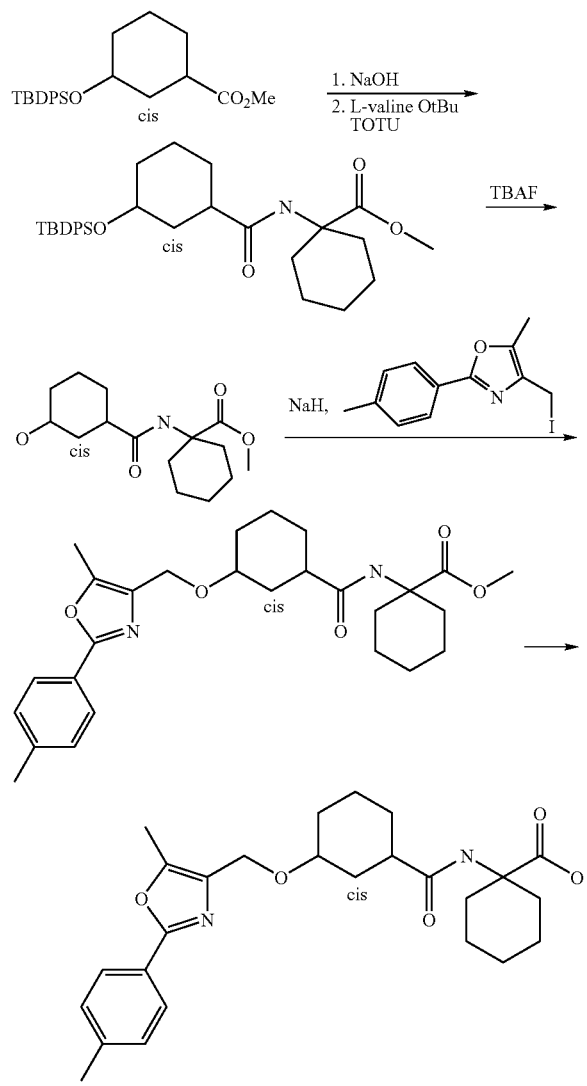

Analogously to Example 1, (1R,3S)/(1S,3R)-3-(tert-butyldiphenylsilanyloxy)cyclohexanecarboxylic acid, methyl 1-aminocyclohexanecarboxylate hydrochloride and 4-iodomethyl-5-methyl-2-p-tolyloxazole gave the racemate methyl 1-{[(1R,3S)/(1S,3R)-3-(5-methyl-2-p-tolyloxazol-4-ylmethoxy)cyclohexanecarbonyl]amino}cyclohexanecarboxylate.
C27H36N2O5 (468.60), ), MS(ESI): 469.

1-{[(1R,3S)/(1S,3R)-3-(5-Methyl-2-p-tolyloxazol-4-ylmethoxy)cyclohexanecarbonyl]amino}cyclohexanecarboxylic acid

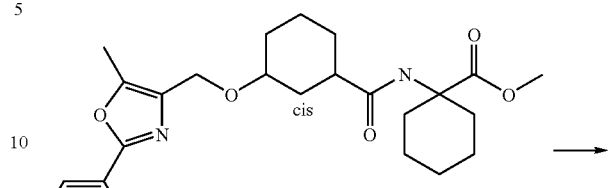

500 mg of the racemate methyl 1-{[(1R,3S)/(1S,3R)-3-(5-methyl-2-p-tolyloxazol-4-ylmethoxy)cyclohexanecarbonyl]amino}cyclohexanecarboxylate are dissolved in 10 ml of tert-butanol, and 1 ml of 10N KOH is added. Under reflux, the mixture is heated at the boil for 1 day. Following neutralization with 2N HCl, the organic phase is separated off and the aqueous phase is extracted three times with in each case 20 ml of ethyl acetate. The combined organic phases are dried over magnesium sulfate, and the solvents are then removed under reduced pressure. The resulting residue is purified by RP-HPLC. This gives 170 mg of 1-{[(1R,3S)/(1S,3R)-3-(5-methyl-2-p-tolyloxazol-4-ylmethoxy)cyclohexanecarbonyl]amino}cyclohexanecarboxylic acid as a colorless lyophilizate. C26H34N2O5 (454.47), MS(ESI): 455 (M+H$^+$).

EXAMPLE 25

1-{[(1R,3S)/(1S,3R)-3-(5-Methyl-2-p-tolyloxazol-4-ylmethoxy)cyclohexanecarbonyl]amino}cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-5-methyl-2-p-tolyloxazole gave the racemate 1-{[(1R,3S)/(1S,3R)-3-(5-methyl-2-p-tolyloxazol-4-ylmethoxy)cyclohexanecarbonyl]amino}cyclopentanecarboxylic acid.

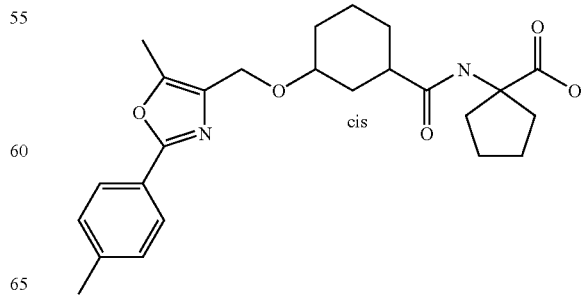

C25H32N2O5 (440.54), MS(ESI): 441 (M+H$^+$).

EXAMPLE 26

1-({(1R,3S)/(1S,3R)-3-[2-(3-Methoxyphenyl)-5-methyloxazol-4-ylmethoxy]-cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-2-(3-methoxyphenyl)-5-methyloxazole gave the racemate 1-({(1R,3S)/(1S,3R)-3-[2-(3-methoxyphenyl)-5-methyloxazol-4-ylmethoxy]cyclohexanecarbonyl}amino)cyclopentanecarboxylic acid.

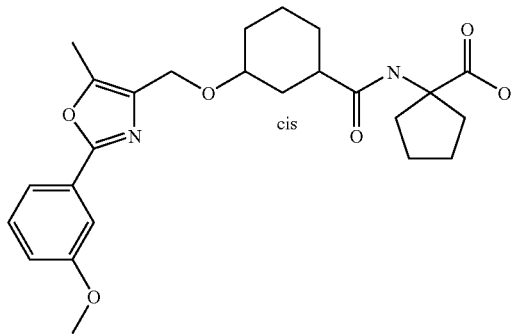

C25H32N2O6 (456.54), MS(ESI): 457 (M+H$^+$).

EXAMPLE 27

1-({(1R,3S)/(1S,3R)-3-[5-Methyl-2-(3-trifluoromethylphenyl)oxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-2-(3-trifluoromethylphenyl)-5-methyloxazole gave the racemate 1-({(1R,3S)/(1S,3R)-3-[5-methyl-2-(3-trifluoromethylphenyl)oxazol-4-ylmethoxy]cyclohexanecarbonyl}amino)cyclopentanecarboxylic acid.

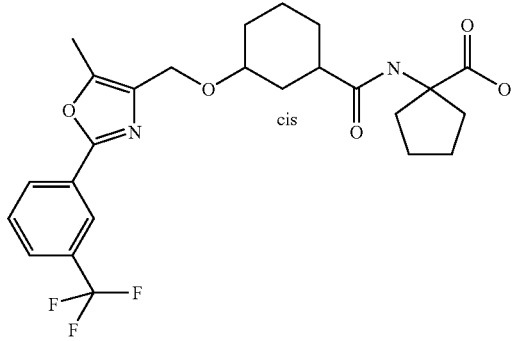

C25H29F3N2O5 (494.52), MS(ESI): 495 (M+H$^+$).

EXAMPLE 28

3-Methyl-2-{methyl-[(1R,3S)/(1S,3R)-(5-methyl-2-p-tolyloxazol-4-ylmethoxy)cyclohexanecarbonyl]amino}butyric acid

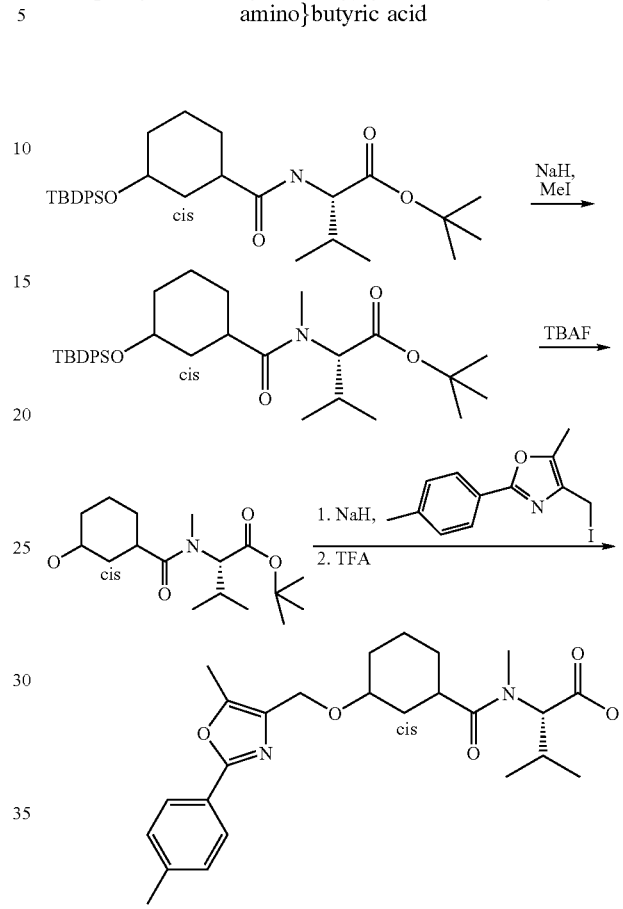

tert-Butyl 2-{[(1R,3S)/(1S,3R)-3-(tert-butyldiphenylsilanyloxy)cyclohexanecarbonyl]methylamino}-3-methylbutyrate

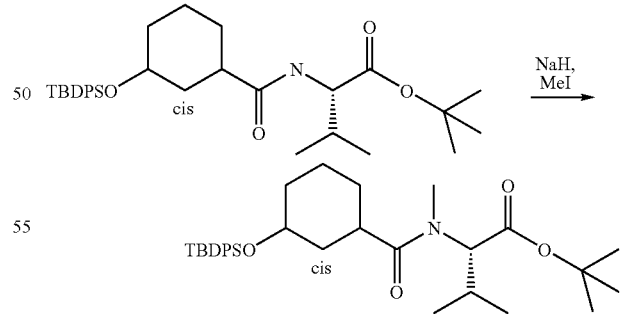

220 mg of sodium hydride (60% strength in paraffin oil) are suspended in 20 ml of dimethylformamide. 2 g of the diastereomer mixture tert-butyl 2-{[(1R,3S)/(1S,3R)-3-(tert-butyldiphenylsilanyloxy)cyclohexanecarbonyl]-amino}-(3S)-methylbutyrate, dissolved in 10 ml of dimethylformamide, are added to this suspension. The mixture is stirred at room temperature for 15 minutes, and 0.5 ml of methyl iodide are then added dropwise. After 2 hours of stirring at room temperature, the reaction mixture is diluted with 200 ml of ethyl acetate and washed three times with water and saturated NaCl solution. The combined organic phases are dried over MgSO4 and the solvent is then removed under reduced pressure. This gives 2.3 g of tert-butyl 2-{[(1R,3S)/(1S,3R)-3-(tert-butyldiphenylsilanyloxy)cyclohexanecarbonyl]methylamino)-3-methylbutyrate as a yellow oil. C33H49NO4Si (551.85), MS(ESI): 552 (M+H+).

tert-Butyl 2-[(1R,3S)/(1S,3R)-3-hydroxycyclohexanecarbonyl)methylamino]-3-methylbutyrate

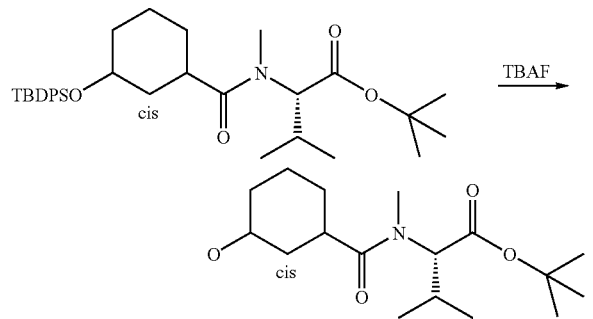

2.3 g of the diastereomer mixture tert-butyl 2-{[(1R,3S)/(1S,3R)-3-(tert-butyldiphenylsilanyloxy)cyclohexanecarbonyl]methylamino}-3-methylbutyrate are dissolved in 10 ml of tetrahydrofuran, and 6 ml of a 1M solution of tetrabutylammonium fluoride in tetrahydrofuran are added. The mixture is stirred at 60° C. for 2 hours and then concentrated under reduced pressure, and the residue is purified on silica gel using the mobile phase n-heptane:ethyl acetate=2:1=>ethyl acetate. This gives 970 mg of tert-butyl 2-[((1R,3S)/(1S,3R)-3-hydroxycyclohexanecarbonyl)methylamino]-3-methylbutyrate as a yellow oil. C17H31NO4 (313.44), MS(ESI): 314 (M+H+), Rf(n-heptane:ethyl acetate=1:1)=0.18.

3-Methyl-2-{methyl-[(1R,3S)/(1S,3R)-(5-methyl-2-p-tolyloxazol-4-ylmethoxy)cyclohexanecarbonyl]amino}butyric acid

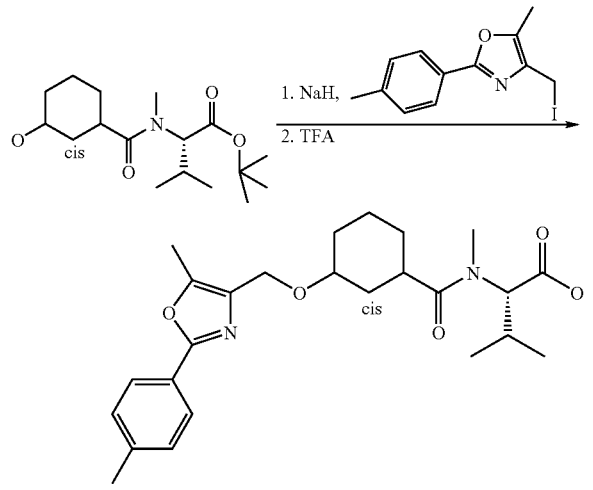

150 mg of sodium hydride (60% strength in paraffin oil) are suspended in 5 ml of dimethylformamide. 970 mg of the diastereomer mixture tert-butyl 2-[(1R,3S)/(1S,3R)-3-hydroxycyclohexanecarbonyl)methylamino]-3-methylbutyrate, dissolved in 10 ml of dimethylformamide, are added to this suspension. The mixture is stirred at room temperature for 15 minutes, and 1.5 g of 4-iodomethyl-5-methyl-2-p-tolyloxazole, dissolved in 10 ml of dimethylformamide, are then added dropwise. After 2 hours of stirring at room temperature, the reaction mixture is diluted with 200 ml of methyl tert-butyl ether and washed three times with water and saturated NaCl solution. The combined organic phases are dried over MgSO4, and the solvent is then removed under reduced pressure. The resulting residue is dissolved in 10 ml of dichloromethane, and 5 ml of trifluoroacetic acid are added. The mixture is stirred at room temperature for 2 hours. 50 ml of toluene are then added, and the solvents are removed under reduced pressure. The residue is purified by RP-HPLC. Freeze-drying gives 105 mg of 3-methyl-2-{methyl-[(1R,3S)/(1S,3R)-(5-methyl-2-p-tolyloxazol-4-ylmethoxy)cyclohexanecarbonyl]amino}butyric acid as a white lyophilizate. C25H34N2O5 (442.56), MS(ESI): 443 (M+H+).

EXAMPLE 29

(S)-2-{Benzyl-[(1R,3S)/(1S,3R)-3-(5-methyl-2-p-tolyloxazol-4-ylmethoxy)cyclohexanecarbonyl]amino}-3-methylbutyric acid Analogously to Example 28, the diastereomer mixture tert-butyl 2-{[(1R,3S)/(1S,3R)-3-(tert-butyldiphenylsilanyloxy)cyclohexanecarbonyl]-amino}-(3S)-methylbutyrate, benzyl bromide and 4-iodomethyl-5-methyl-2-p-tolyloxazole gave the diastereomer mixture (S)-2-{benzyl-[(1R,3S)/(1S,3R)-3-(5-methyl-2-p-tolyloxazol-4-ylmethoxy)cyclohexanecarbonyl]amino}-3-methylbutyric acid.

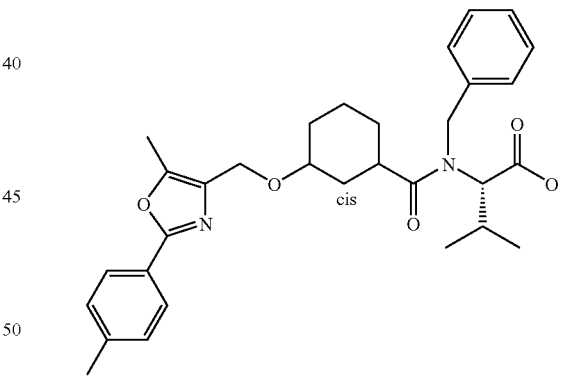

C31H38N2O5 (518.66), (MS(ESI): 519 (M+H+).

EXAMPLE 30

(S)-3-Methyl-2-{[(1R,3S)/(1S,3R)-3-(5-methyl-2-p-tolyloxazol-4-ylmethoxy)cyclohexanecarbonyl]propylamino}butyric acid Analogously to Example 28, the diastereomer mixture tert-butyl 2-{[(1R,3S)/(1S,3R)-3-(tert-butyldiphenylsilanyloxy)cyclohexanecarbonyl]-amino}-(3S)-methylbutyrate and allyl bromide gave the diastereomer mixture tert-butyl 2-[allyl-((1R,3S)/(1S,3R)-3-hydroxycyclohexanecarbonyl)-amino]-3-methylbutyrate.

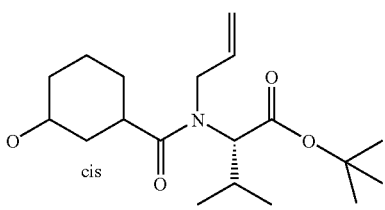

C19H33NO4 (339.48), MS(ESI): 340 (M+H+).

tert-Butyl 2-[((1R,3S)/(1S,3R)-3-hydroxycyclohexanecarbonyl)propylamino]-3-methylbutyrate

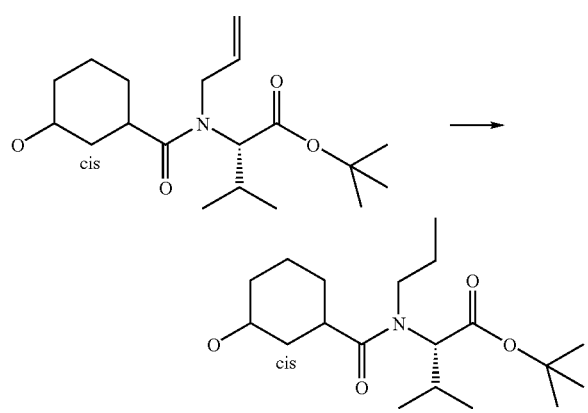

1 g of the diastereomer mixture tert-butyl 2-[allyl-((1R,3S)/(1S,3R)-3-hydroxycyclohexanecarbonyl)amino]-3-methylbutyrate is dissolved in 30 ml of methanol, and 100 mg of palladium (10% on carbon) are added. The mixture is stirred under a hydrogen atmosphere at 5 bar for 3 h. The mixture is then filtered through Celite, and the solvent is removed under reduced pressure. This gives 1 g of tert-butyl 2-[((1R,3S)/(1S,3R)-3-hydroxycyclohexanecarbonyl)propylamino]-3-methylbutyrate as a colorless oil. C19H35NO4 (341.50), MS(ESI): 342 (M+H+).

Analogously to Example 28, the diastereomer mixture tert-butyl 2-[((1R,3S)/(1S,3R)-3-hydroxycyclohexanecarbonyl)propylamino]-3-methylbutyrate and 4-iodomethyl-5-methyl-2-p-tolyloxazole gave the diastereomer mixture (S)-3-methyl-2-{[(1R,3S)/(1R,3S)-3-(5-methyl-2-p-tolyloxazol-4-ylmethoxy)cyclohexanecarbonyl]propylamino}butyric acid.

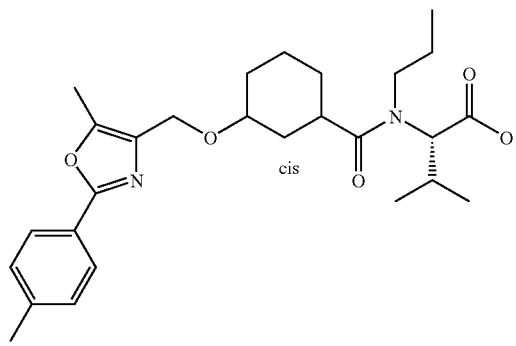

C27H38N2O5 (470.61), MS(ESI): 342 (M+H+).

EXAMPLE 31

1-{[(1R,3S)/(1S,3R)-3-(5-Ethyl-2-p-tolyloxazol-4-ylmethoxy)cyclohexanecarbonyl]amino}cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-5-ethyl-2-p-tolyloxazole gave the racemate 1-{[(1R,3S)/(1S,3R)-3-(5-ethyl-2-p-tolyloxazol-4-ylmethoxy)cyclohexanecarbonyl]amino}cyclopentanecarboxylic acid.

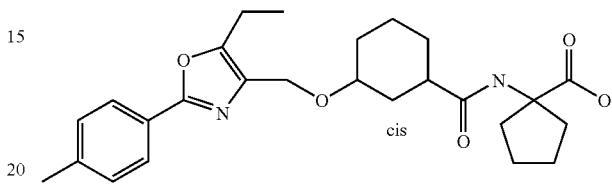

C26H34N2O5 (454.57), MS(ESI): 455(M+H+).

EXAMPLE 32

1-{[(1R,3S)/(1S,3R)-3-[2-(3,5-Dimethoxyphenyl)-5-methyloxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 2-(3,5-dimethoxyphenyl)-4-iodomethyl-5-methyloxazole gave the racemate 1-{[(1R,3S)/(1S,3R)-3-[2-(3,5-dimethoxyphenyl)-5-methyloxazol-4-ylmethoxy]cyclohexanecarbonyl}-amino)cyclopentanecarboxylic acid.

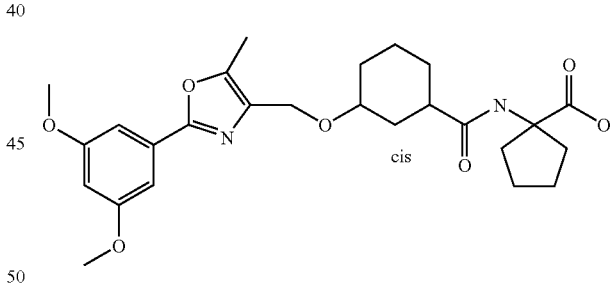

C26H34N2O7 (486.57), MS(ESI): 487(M+H+).

EXAMPLE 33

1-{[(1R,3S)/(1S,3R)-({3-[5-Isopropyl-2-(3-trifluoromethylphenyl)oxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-5-isopropyl-2-(3-trifluoromethylphenyl)oxazole gave the racemate 1-{[(1R,3S)/(1S,3R)-({3-[5-isopropyl-2-(3-trifluoromethylphenyl)oxazol-4-ylmethoxy]cyclohexanecarbonyl}amino)cyclopentanecarboxylic acid.

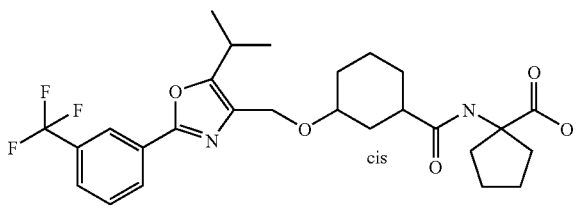

C27H33F3N2O5 (522.57), MS(ESI): 523(M+H$^+$).

EXAMPLE 34

1-{[(1R,3S)/(1S,3R)-({3-[5-Ethyl-2-(3-trifluoromethylphenyl)oxazol-4-ylmethoxy]cyclohexanecarbonyl}amino)cyclopentanecarboxylic acid Analogously to Example 24, (1R,3S)/(1S,3R)-3-(tert-butyidiphenylsilanyloxy)cyclohexanecarboxylic acid, methyl 1-aminocyclopentanecarboxylate hydrochloride and 5-ethyl-4-iodomethyl-2-(3-trifluoromethylphenyl)oxazole gave the racemate 1-{[(1R,3S)/(1S,3R)-({3-[5-ethyl-2-(3-trifluoromethylphenyl)oxazol-4-ylmethoxy]cyclohexanecarbonyl}amino)cyclopentanecarboxylic acid.

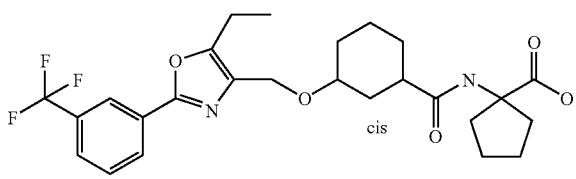

C26H31F3N2O5 (508.54), MS(ESI): 509(M+H$^+$).

EXAMPLE 35

1-{[(1R,3S)/(1S,3R)-({3-[2-(3,4-Dimethylphenyl)-5-isopropyloxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 2-(3,4-dimethylphenyl)-4-iodomethyl-5-isopropyloxazole gave the racemate 1-{[(1R,3S)/(1S,3R)-({3-[2-(3,4-dimethylphenyl)-5-isopropyloxazol-4-ylmethoxy]cyclohexanecarbonyl}amino)cyclopentanecarboxylic acid.

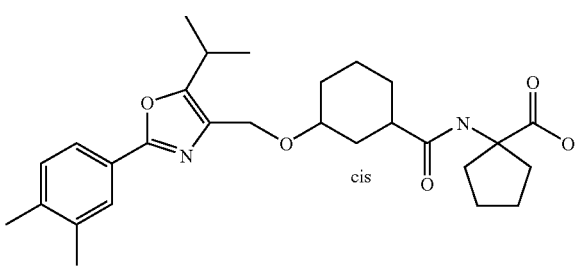

C28H38N2O5 (482.63), MS(ESI): 483(M+H$^+$).

EXAMPLE 36

1-{[(1R,3S)/(1S,3R)-({3-[2-(4-Methoxyphenyl)-5-methyloxazol-4-ylmethoxy]-cyclohexanecarbonyl}amino)cyclopentanecarboxylic acid Analogously to Example 24, (1R,3S)/(1S,3R)-3-(tert-butyidiphenylsilanyloxy)cyclohexanecarboxylic acid, methyl 1-aminocyclopentanecarboxylate hydrochloride and 4-iodomethyl-2-(4-methoxyphenyl)-5-methyloxazole gave the racemate 1-{[(1R,3S)/(1S,3R)-({3-[2-(4-methoxyphenyl)-5-methyloxazol-4-ylmethoxy]cyclohexanecarbonyl}amino)cyclopentanecarboxylic acid.

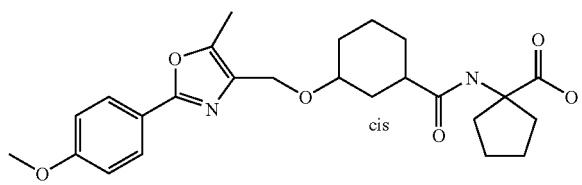

C25H32N2O6 (456.54), MS(ESI): 457(M+H$^+$).

EXAMPLE 37

1-{[(1R,3S)/(1S,3R)-{[3-(5-Ethyl-2-naphthalen-2-yloxazol-4-ylmethoxy)cyclohexanecarbonyl]amino}cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 5-ethyl-4-iodomethyl-2-naphthalen-2-yloxazole gave the racemate 1-{[(1R,3S)/(1S,3R)-{[3-(5-ethyl-2-naphthalen-2-yloxazol-4-ylmethoxy)cyclohexanecarbonyl]amino}cyclopentanecarboxylic acid.

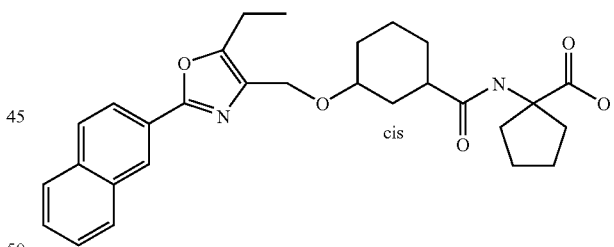

C29H34N2O5 (490.60), MS(ESI): 491(M+H$^+$).

EXAMPLE 38

1-{[(1R,3S)/(1S,3R)-({3-[5-Ethyl-2-(3-methoxyphenyl)oxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 5-ethyl-4-iodomethyl-2-(3-methoxyphenyl)oxazole gave the racemate 1-{[(1R,3S)/(1S,3R)-({3-[5-ethyl-2-(3-methoxyphenyl)oxazol-4-ylmethoxy]cyclohexanecarbonyl}amino)cyclopentanecarboxylic acid.

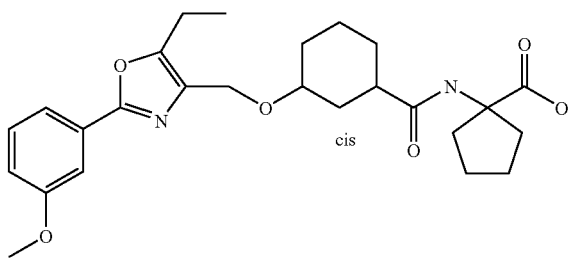

C26H34N2O6 (470.57), MS(ESI): 471 (M+H+).

EXAMPLE 39

1-{[(1R,3S)/(1S,3R)-({3-[2-(4-Isopropylphenyl)-5-methyloxazol-4-ylmethoxy]cyclohexanecarbonyl}amino)cyclolentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 4-iodomethyl-2-(4-isopropylphenyl)-5-methyloxazole gave the racemate 1-{[(1R,3S)/(1S,3R)-({3-[2-(4-isopropylphenyl)-5-methyloxazol-4-ylmethoxy]cyclohexanecarbonyl}amino) cyclopentanecarboxylic acid.

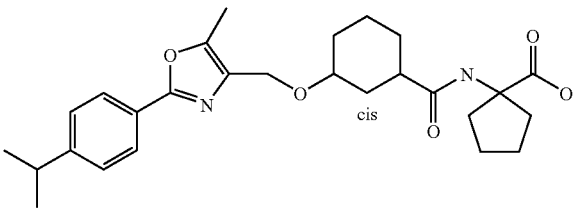

C27H36N2O5 (468.60), MS(ESI): 469(M+H+).

EXAMPLE 40

1-{[(1R,3S)/(1S,3R)-({3-[5-Ethyl-2-(4-isopropylphenyl)oxazol-4-ylmethoxy]cyclohexanecarbonyl}amino)cyclopentanecarboxylic acid Analogously to Example 24, (1R,3S)/(1S,3R)-3-(tert-butyldiphenylsilanyloxy)cyclohexanecarboxylic acid, methyl 1-aminocyclopentanecarboxylate hydrochloride and 5-ethyl-4-iodomethyl-2-(4-isopropylphenyl)oxazole gave the racemate 1-{[(1R,3S)/(1S,3R)-({3-[5-ethyl-2-(4-isopropylphenyl)oxazol-4-ylmethoxy]cyclohexanecarbonyl}amino)cyclopentanecarboxylic acid.

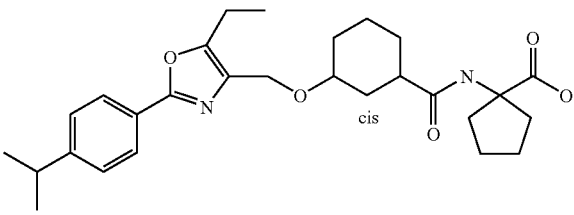

C28H38N2O5 (482.63), MS(ESI): 483(M+H+).

EXAMPLE 41

(S)-(3-Methyl-2-{[(1R,3S)/(1S,3R)-3-(5-methyl-2-p-tolyloxazol-4-ylmethoxymethyl)cyclohexanecarbonyl]amino}butyric acid (S)-(1R,3S)/(1S,3R)-3-(1-tert-Butoxycarbonyl-2-methylpropylcarbamoyl)cyclohexanecarboxylic acid

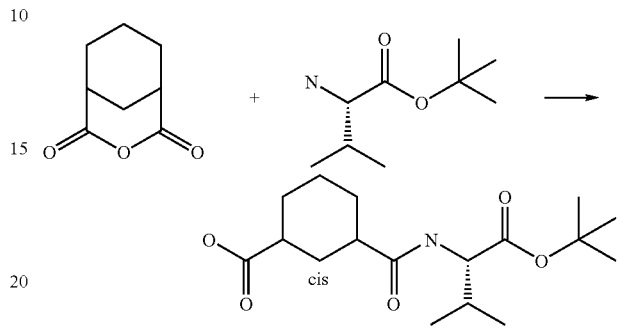

At 0° C., 5.0 g of 3-oxabicyclo[3.3.1]nonane-2,4-dione and 7.1 g of tert-butyl L-valinate hydrochloride are initially charged in 50 ml of dimethylformamide, and 4.5 ml of triethylamine and a spatula tip of dimethylaminopyridine are added. The reaction mixture is stirred at room temperature for one hour and then diluted by addition of 200 ml of ethyl acetate and washed five times with water, 1 N hydrochloric acid and saturated sodium chloride solution. The organic phase is dried over magnesium sulfate and the solvent is then removed under reduced pressure. The residue obtained are 7.0 g of the desired diastereomer mixture (S)-(1R,3S)/(1S,3R)-3-(1-tert-butoxycarbonyl-2-methylpropylcarbamoyl) cyclohexanecarboxylic acid as a colorless oil.

C17H29NO5 (327.42), MS(ESI): 272 (M-tert-butyl+2H+).

tert-Butyl (S)-(2-[((1R,3S)/(1S,3R)-3-hydroxymethylcyclohexanecarbonyl)amino]-3-methylbutyrate

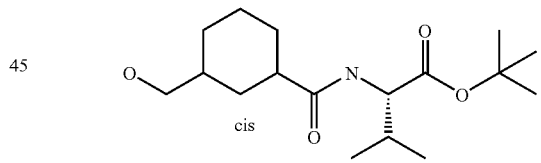

7.0 g of (S)-(1R,3S)/(1S,3R)-3-(1-tert-butoxycarbonyl-2-methylpropylcarbamoyl)cyclohexanecarboxylic acid are dissolved in 200 ml of tetrahydrofuran, and 4.05 ml of triethylamine are added. The reaction mixture is stirred at room temperature for one hour and then cooled to −78° C., and 3.58 ml of isobutyl chloroformate are added. The reaction mixture is allowed to warm to room temperature overnight and filtered through celite, and the filter cake is washed with a little cold tetrahydrofuran. With ice cooling, 2.75 g of sodium borohydride are added to the filtrate, followed by the dropwise addition of 10 ml of water. After two hours of stirring at room temperature, the reaction mixture is filtered through celite and the filtrate is concentrated under reduced pressure. The residue is extracted three times with in each case 150 ml of ethyl acetate, the combined organic extracts are dried over magnesium sulfate and the solvent is then removed under reduced pressure. The residue obtained are 6.7 g of the desired diastereomer mixture tert-butyl (S)-(2-[((1R,3S)/(1S,3R)-3-hydroxymethylcyclohexanecarbonyl)amino]-3-methylbutyrate as a colorless oil.

C17H31NO4 (313.44), MS(ESI): 258 (M-tert-butyl+2H$^+$).

tert-Butyl (S)-(3-methyl-2-{[(1R,3S)/(1S,3R)-3-(5-methyl-2-p-tolyloxazol-4-ylmethoxymethyl)cyclohexanecarbonyl]amino}butyrate

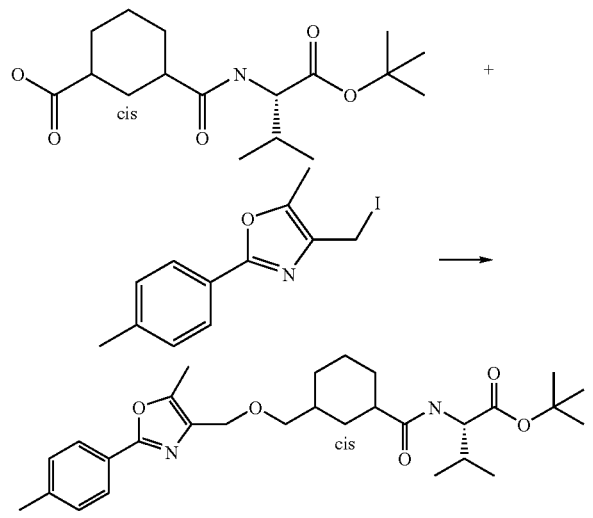

200 mg of tert-butyl (S)-(2-[((1R,3S)/(1S,3R)-3-hydroxymethylcyclohexanecarbonyl)amino]-3-methylbutyrate and 260 mg of 4-iodomethyl-5-methyl-2-p-tolyloxazole ae dissolved in 30 ml of chlorobenzene, and 86 mg of potassium tert-butoxide are added. The reaction mixture is stirred at room temperature for one hour, 100 ml of ethyl acetate are then added and the reaction mixture is washed with 40 ml of a 1M hydrochloric acid solution and three times with in each case 50 ml of saturated sodium chloride solution. The organic phase is dried over magnesium sulfate and the solvent is then removed under reduced pressure. The residue is purified by HPLC. Freeze-drying gives 150 mg of the desired diastereomer mixture tert-butyl (S)-(3-methyl-2-{[(1R,3S)/(1S,3R)-3-(5-methyl-2-p-tolyloxazol-4-ylmethoxymethyl)cyclohexanecarbonyl]amino}butyrate as a yellow oil.

C29H42N2O5 (498.67), MS(ESI): 499 (M+H$^+$).

(S)-(3-Methyl-2-{[(1R,3S)/(1S,3R)-3-(5-methyl-2-p-tolyloxazol-4-ylmethoxymethyl)cyclohexanecarbonyl]amino}butyrate

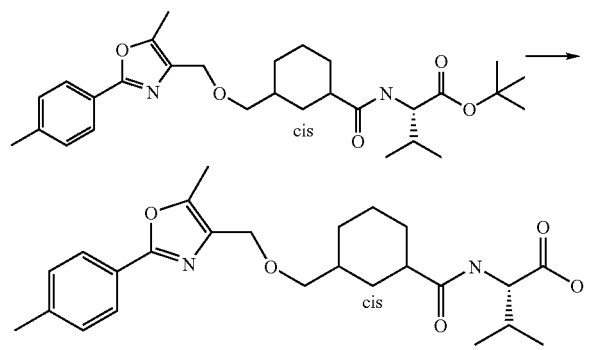

150 mg of tert-butyl (S)-(3-methyl-2-{[(1R,3S)/(1S,3R)-3-(5-methyl-2-p-tolyloxazol-4-ylmethoxymethyl)cyclohexanecarbonyl]amino}butyrate are dissolved in 10 ml of dichloromethane, and 2 ml of trifluoroacetic acid are added. After two hours of stirring at room temperature, 50 ml of toluene are added and the solvents are removed under reduced pressure. The resulting residue is taken up in water and lyophilized. This gives 130 mg of the desired diastereomer mixture (S)-(3-methyl-2-{[(1R,3S)/(1S,3R)-3-(5-methyl-2-p-tolyloxazol-4-ylmethoxymethyl)cyclohexanecarbonyl]amino}-butyric acid as a white solid.

C25H34N2O5 (442.56), MS(ESI): 443 (M+H$^+$).

EXAMPLE 42

(S)-(2-({(1R,3S)/(1S,3R)-3-[2-(3,4-Dimethylphenyl)-5-ethyloxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 2-(3,4-dimethylphenyl)-5-ethyl-4-iodomethyloxazole gave the diastereomer mixture (S)-(2-({(1R,3S)/(1S,3R)-3-[2-(3,4-dimethylphenyl)-5-ethyloxazol-4-ylmethoxymethyl]cyclohexanecarbonyl}amino)-3-methylbutyric acid.

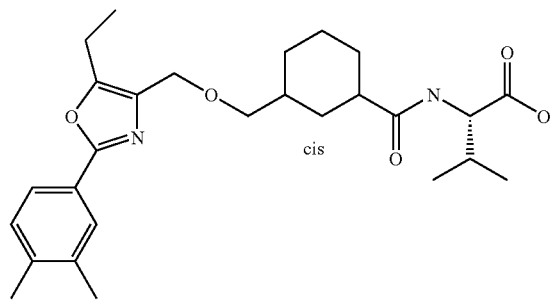

C27H38N2O5 (470.61), MS(ESI): 471 (M+H$^+$).

EXAMPLE 43

(S)-(2-({1,3-(1R,3S)/(1S,3R)-3-[5-Isopropyl-2-(4-trifluoromethylphenyl)oxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 4-iodomethyl-5-isopropyl-2-(4-trifluoromethylphenyl)oxazole gave the diastereomer mixture (S)-(2-({1,3-(1R,3S)/(1S,3R)-3-[5-isopropyl-2-(4-trifluoromethylphenyl)oxazol-4-ylmethoxymethyl]cyclohexanecarbonyl}amino)-3-methylbutyric acid.

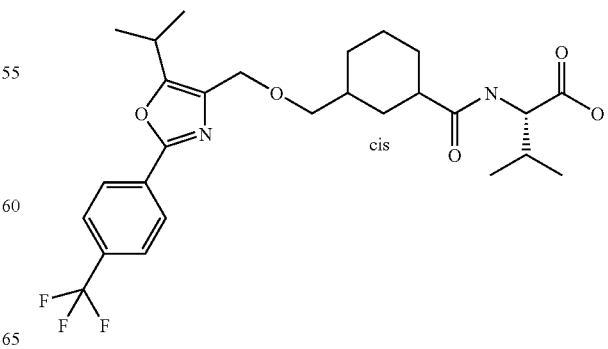

C27H35F3N2O5 (524.59), MS(ESI): 525 (M+H$^+$).

EXAMPLE 44

(S)-(3-Methyl-2-({(1R,3S)/(1S,3R)-3-[5-methyl-2-(3-trifluoromethylphenyl)oxazol-4-ylmethoxymethyl]cyclohexanecarbonyl}amino)butyric acid Analogously to Example 41, 3-oxabicyclo[3.3.1]nonane-2,4-dione, tert-butyl L-valinate hydrochloride and 4-iodomethyl-5-methyl-2-(3-trifluoromethylphenyl)oxazole gave the diastereomer mixture (S)-(3-methyl-2-({(1R,3S)/(1S,3R)-3-[5-methyl-2-(3-trifluoromethylphenyl)oxazol-4-ylmethoxymethyl]cyclohexanecarbonyl}amino)butyric acid.

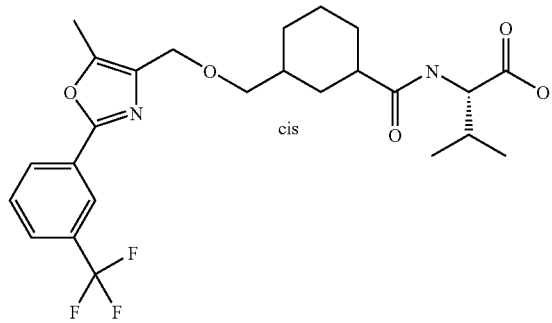

C25H31F3N2O5 (496.53), MS(ESI): 497 (M+H$^+$).

EXAMPLE 45

(S)-2-({(1R,3S)/(1S,3R)-3-[5-Ethyl-2-(4-isoproyylphenyl)oxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 5-ethyl-4-iodomethyl-2-(4-isopropylphenyl)oxazole gave the diastereomer mixture (S)-2-({(1R,3S)/(1S,3R)-3-[5-ethyl-2-(4-isopropylphenyl)oxazol-4-ylmethoxymethyl]cyclohexanecarbonyl}amino)-3-methylbutyric acid.

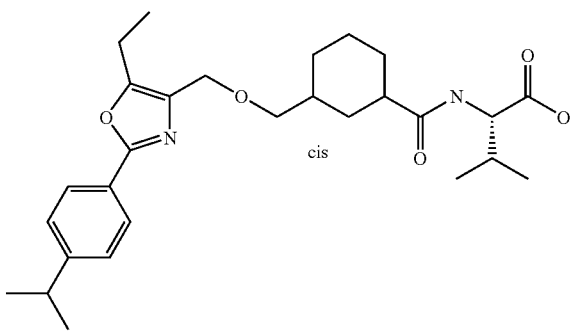

C28H40N2O5 (484.64), MS(ESI): 485 (M+H$^+$).

EXAMPLE 46

(S)-(2-{[(1R,3S)/(1S,3R)-3-(5-Ethyl-2-p-tolyloxazol-4-ylmethoxymethyl)cyclohexanecarbonyl]amino}-3-methylbutyric acid Analogously to Example 41, 3-oxabicyclo[3.3.1]nonane-2,4-dione, tert-butyl L-valinate hydrochloride and 5-ethyl-4-iodomethyl-2-p-tolyloxazole gave the diastereomer mixture (S)-(2-{[(1R,3S)/(1S,3R)-3-(5-ethyl-2-p-tolyloxazol-4-ylmethoxymethyl)cyclohexanecarbonyl]amino}-3-methylbutyric acid.

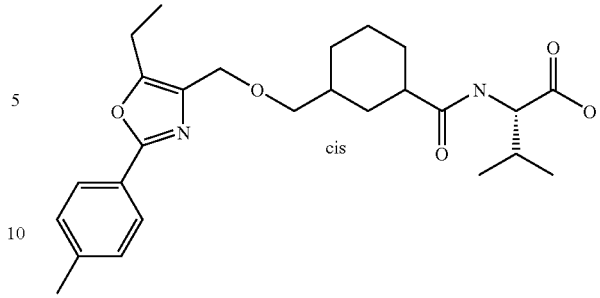

C26H36N2O5 (456.59), MS(ESI): 457 (M+H$^+$).

EXAMPLE 47

(S)-(2-({(1R,3S)/(1S,3R)-3-[5-Cyclohexyl-2-(3-methoxyphenyl)oxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 5-cyclohexyl-4-iodomethyl-2-(3-methoxyphenyl)oxazole gave the diastereomer mixture (S)-(2-({(1R,3S)/(1S,3R)-3-[5-cyclohexyl-2-(3-methoxyphenyl)oxazol-4-ylmethoxymethyl]cyclohexanecarbonyl}amino)-3-methylbutyric acid.

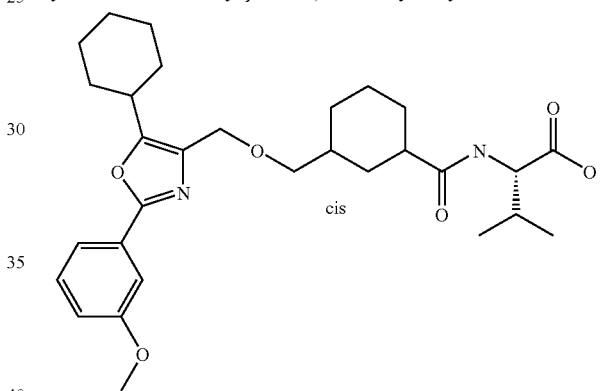

C30H42N2O6 (526.68), MS(ESI): 527 (M+H$^+$).

EXAMPLE 48

(S)-(2-({(1R,3S)/(1S,3R)-3-[2-(3-Methoxyphenyl)-5-methyloxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 4-iodomethyl-2-(3-methoxyphenyl)-5-methyloxazole gave the diastereomer mixture (S)-(2-({(1R,3S)/(1S,3R)-3-[2-(3-methoxyphenyl)-5-methyloxazol-4-ylmethoxymethyl]cyclohexanecarbonyl}amino)-3-methylbutyric acid.

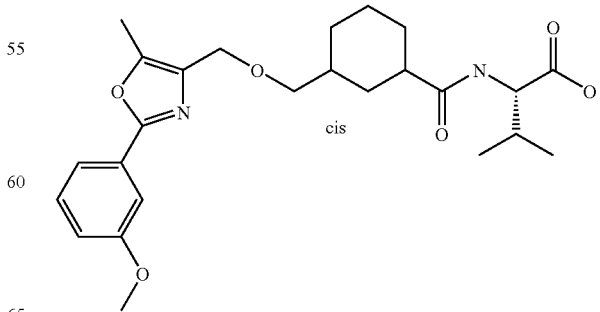

C25H34N2O6 (458.56), MS(ESI): 459 (M+H$^+$).

EXAMPLE 49

(S)-(2-({3-[2-(4-Isopropylphenyl)-5-methyloxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 4-iodomethyl-2-(4-isopropylphenyl)-5-methyloxazole gave the diastereomer mixture (S)-(2-({3-[2-(4-isopropylphenyl)-5-methyloxazol-4-ylmethoxymethyl]cyclohexanecarbonyl}amino)-3-methylbutyric acid.

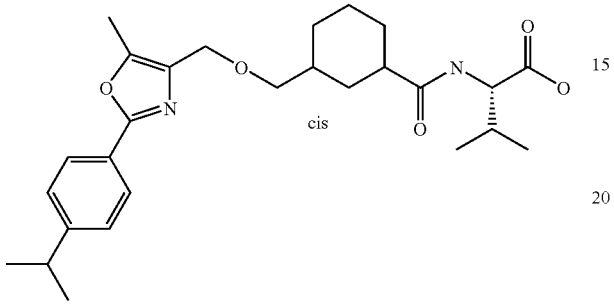

C27H38N2O5 (470.61), MS(ESI): 471 (M+H$^+$).

EXAMPLE 50

(S)-(2-({(1R,3S)/(1S,3R)-3-[2-(4-Trifluoromethylphenyl)-5-ethyloxazol-4-ylmethoxymethyl]cyclohexanecarbonyl}amino)-3-methylbutyric acid Analogously to Example 41, 3-oxabicyclo[3.3.1]nonane-2,4-dione, tert-butyl L-valinate hydrochloride and 5-ethyl-4-iodomethyl-2-(4-trifluoromethylphenyl)oxazole gave the diastereomer mixture (S)-(2-({(1R,3S)/(1S,3R)-3-[2-(4-trifluoromethylphenyl)-5-ethyloxazol-4-ylmethoxymethyl]cyclohexanecarbonyl}amino)-3-methylbutyric acid.

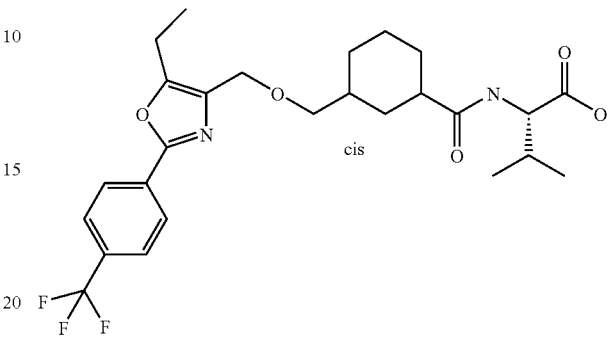

C26H33F3N2O5 (510.56), MS(ESI): 511 (M+H$^+$).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A compound having the formula I

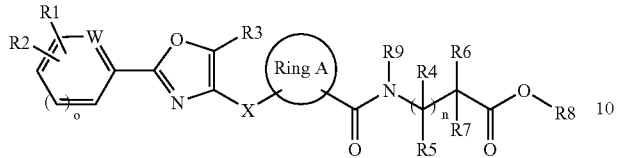

in which:
- Ring A is $(C_3-C_8)$-cycloalkanediyl or $(C_3-C_8)$-cycloalkenediyl;
- R1, R2 independently of one another are H, F, Cl, Br, $CF_3$, $OCF_3$, $(C_1-C_6)$-alkyl, O—$(C_1-C_6)$-alkyl, $SCF_3$, $SF_5$, $OCF_2$—$CHF_2$, $(C_6-C_{10})$-aryl, $(C_6-C_{10})$-aryloxy, OH, $NO_2$; or
- R1 and R2 together with the phenyl ring form fused, partially or unsaturated bicyclic $(C_6-C_{10})$-aryl;
- R3 is H, $(C_1-C_6)$-alkyl, $(C_3-C_8)$-cycloalkyl, $(C_1-C_3)$-alkyl-$(C_3-C_8)$-cycloalkyl, phenyl, $(C_1-C_3)$-alkyl-phenyl, or (C1-C3)-alkyl which is fully or partially substituted by F;
- W is CH;
- o is 1;
- X is $(C_1-C_6)$-alkanediyl, where in the alkanediyl group one or more carbon atoms may be replaced by oxygen atoms;
- n is 0-2;
- R4 is H or $(C_1-C_6)$-alkyl;
- R5 is H or $(C_1-C_6)$-alkyl;
- R6 is H, $(C_1-C_6)$-alkyl or F;
- R7 is H; F; $(C_1-C_6)$-alkoxy; $(C_2-C_6)$-alkenyl; $(C_2-C_6)$-alkynyl; $(C_3-C_8)$-cycloalkyl; phenyl which may be unsubstituted or substituted by one or more radicals from the group consisting of hydroxy, $(C_1-C_6)$-alkoxy, F and $CF_3$; $(C_1-C_6)$-alkyl which may be unsubstituted or substituted by one or more radicals selected from the group consisting of hydroxyl, phenyl, $(C_1-C_6)$-alkoxy and NR11R12;
  with the proviso that R7 is not NR11 R12 or $(C_1-C_6)$-alkoxy if R6=F;
- R7 and R9 together with the atoms that carry them are pyrrolidine if n=0;
- R6 and R7 together with the carbon atom that carries them are $(C_3-C_8)$-cycloalkyl;
- R8 is H, $(C_1-C_6)$-alkyl;
- R9 is H, $(C_1-C_6)$-alkyl, $(C_2-C_6)$-alkenyl, $(C_2-C_6)$-alkynyl, $(C_1-C_4)$-alkyl-$(C_6-C_{10})$-aryl, $(C_1-C_4)$-alkyl-O—$(C_1-C_4)$-alkyl, phenyl-$(C_1-C_4)$-alkyl;
- R10 is H, $(C_1-C_6)$-alkyl-phenyl, $(C_1-C_6)$-alkyl;
- R11 is H, $(C_1-C_6)$-alkyl-phenyl, $(C_1-C_6)$-alkyl;
- R12 is H, $(C_1-C_6)$-alkyl-phenyl, $(C_1-C_6)$-alkyl;
- a physiologically acceptable salt of the compound;
- a solvate of the compound; or
- a physiologically effective derivative of the compound.

2. The compound of claim 1, in which
- Ring A is $(C_3-C_8)$-cycloalkanediyl or $(C_3-C_8)$-cycloalkenediyl;
- X is $(C_1-C_6)$-alkanediyl, wherein the C1 or C2 carbon atom (to Ring A) of the alkanediyl group may be replaced by an oxygen atom.

3. The compound of claim 1, in which
- Ring A is cis-cyclohexane-1,3-diyl
- R1 is Br, $CF_3$, $OCF_3$, $(C_1-C_6)$-alkyl, O—$(C_1-C_6)$-alkyl;
- R2 is H, (C1-C6)-alkyl, O—(C1-C6)-alkyl or
- R1 and R2 together with the phenyl ring form naphthyl;
- R3 is $CF_3$, $(C_1-C_6)$-alkyl, $(C_3-C_8)$-cycloalkyl, phenyl;
- W is CH;
- o is 1;
- X is $CH_2O$ or $CH_2$—O—$CH_2$;
- n is 0;
- R6 is H or $(C_1-C_6)$-alkyl;
- R7 is $(C_1-C_6)$-alkyl, where alkyl may be unsubstituted or substituted by phenyl;
- R7 and R9 together with the atoms that carry them are pyrrolidine if n=0;
- R6 and R7 together with the carbon atom that carries them are $(C_3-C_6)$-cycloalkyl;
- R8 is H; and
- R9 is H, $(C_1-C_6)$-alkyl or benzyl.

4. A pharmaceutical composition, comprising the compound of claim 1 and a pharmaceutically acceptable carrier.

5. The pharmaceutical composition of claim 4, further comprising an active compound having a favorable effect on a metabolic disorder or disease.

6. The pharmaceutical composition of claim 4, further comprising an antidiabetic.

7. The pharmaceutical composition of claim 4, further comprising a lipid modulator.

8. A method for treating a disorder in which insulin resistance is involved in a patient, comprising administering a therapeutically effective amount of the compound of claim 1 to the patient.

9. A method for treating diabetes mellitus and its sequelae in a patient, comprising administering a therapeutically effective amount of the compound of claim 1 to the patient.

10. The method of claim 8, further comprising administering a at least one further active compound for treating a disorder in which insulin is involved.

11. A process for preparing a pharmaceutical comprising the compound of claim 1, comprising the steps of:
   (a) mixing the compound with a pharmaceutically acceptable carrier, and;
   (b) bringing the mixture into a form suitable for administration.

12. A pharmaceutical composition comprising the compound of claim 2 and a pharmaceutically acceptable carrier.

13. A method for treating a disorder in which insulin resistance is involved in a patient, comprising administering a therapeutically effective amount of the compound of claim 2 to the patient.

14. A method for treating diabetes mellitus and its sequelae in a patient, comprising administering a therapeutically effective amount of the compound of claim 2 to the patient.

15. A pharmaceutical composition comprising the compound of claim 3 and a pharmaceutically acceptable carrier.

16. A method for treating a disorder in which insulin resistance is involved in a patient, comprising administering a therapeutically effective amount of the compound of claim 3 to the patient.

17. A method for treating diabetes mellitus and its sequelae in a patient, comprising administering a therapeutically effective amount of the compound of claim 3 to the patient.

* * * * *

UNITED STATES PATENT AND TRADEMARK OFFICE
CERTIFICATE OF CORRECTION

PATENT NO.      : 7,365,084 B2
APPLICATION NO. : 10/788997
DATED           : April 29, 2008
INVENTOR(S)     : Christian Stapper et al.

Page 1 of 1

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (520) days Delete the phrase "by 520 days" and insert -- by 400 days --

Signed and Sealed this

Sixth Day of January, 2009

JON W. DUDAS
*Director of the United States Patent and Trademark Office*